(12) United States Patent
Christoforou et al.

(10) Patent No.: US 10,857,423 B2
(45) Date of Patent: Dec. 8, 2020

(54) HAND THERAPY KIT WITH PRESENCE SENSORS

(71) Applicant: ISOS Solutions LLC, Brooklyn, NY (US)

(72) Inventors: Dimitrios Christoforou, Nissequogue, NY (US); Vipul Patel, New York, NY (US)

(73) Assignee: ISOS Solutions LLC, Brooklyn, NY (US)

( * ) Notice: Subject to any disclaimer, the term of this patent is extended or adjusted under 35 U.S.C. 154(b) by 76 days.

(21) Appl. No.: 16/205,537

(22) Filed: Nov. 30, 2018

(65) Prior Publication Data

US 2019/0091511 A1 Mar. 28, 2019

Related U.S. Application Data

(63) Continuation-in-part of application No. 16/016,098, filed on Jun. 22, 2018, now Pat. No. 10,173,099, (Continued)

(51) Int. Cl.
*A63B 23/16* (2006.01)
*A63B 21/04* (2006.01)
(Continued)

(52) U.S. Cl.
CPC .............. *A63B 23/16* (2013.01); *A61F 7/00* (2013.01); *A61F 7/007* (2013.01); *A61F 7/0053* (2013.01);
(Continued)

(58) Field of Classification Search
CPC .......... A63B 21/4033; A63B 21/00189; A63B 21/0414; A63B 21/0552; A63B 23/03508; A63B 21/4039; A63B 1/0622; A63B 23/03533; A63B 2071/063; A63B 2210/50; A63B 2220/806; A63B 2225/64; A63B 2225/66; A63B 71/0622; A61F 7/00; A61F 7/0053; A61F 7/007; A61F 7/0085; A61F 7/02; A61F 7/03; A61F 13/105; A61F 17/00; A61F 2007/0036; A61F 2007/0078;
(Continued)

(56) References Cited

U.S. PATENT DOCUMENTS 1,472,906 A 11/1923 Gorrell
5,658,224 A 8/1997 Betrock
(Continued)

FOREIGN PATENT DOCUMENTS

WO WO2013126897 A1 8/2013

*Primary Examiner* — Loan B Jimenez
*Assistant Examiner* — Andrew M Kobylarz
(74) *Attorney, Agent, or Firm* — Intrinsic Law Corp.

(57) ABSTRACT

A hand therapy kit includes hand therapy modules and a housing having defined receptacles in which the hand therapy modules are removably disposed. A module presence sensor is disposed in each receptacle to detect the presence or absence of the corresponding hand therapy module. A microprocessor disposed in the hand therapy kit sends the module presence sensor data to a remote computer that analyzes the module presence sensor data to determine whether the patient is complying with a prescribed treatment regimen. The remote computer can generate warnings, alerts, and/or notifications when noncompliance is detected.

29 Claims, 29 Drawing Sheets

Related U.S. Application Data which is a continuation-in-part of application No. 15/348,623, filed on Nov. 10, 2016, now Pat. No. 10,029,146, which is a continuation of application No. 14/640,943, filed on Mar. 6, 2015, now Pat. No. 9,616,287.

(51) Int. Cl.

| | | |
|---|---|---|
| *A63B 21/055* | (2006.01) | |
| *A61F 13/10* | (2006.01) | |
| *A61F 7/00* | (2006.01) | |
| *A63B 21/00* | (2006.01) | |
| *B65D 43/16* | (2006.01) | |
| *G09B 23/28* | (2006.01) | |
| *A63B 23/035* | (2006.01) | |
| *A61H 33/04* | (2006.01) | |
| *A61F 17/00* | (2006.01) | |
| *G09B 19/00* | (2006.01) | |
| *G06Q 50/22* | (2018.01) | |
| *A61F 7/03* | (2006.01) | |
| *A61F 7/02* | (2006.01) | |
| *A61H 7/00* | (2006.01) | |
| *A63B 71/06* | (2006.01) | |
| *A61F 7/10* | (2006.01) | |

(52) U.S. Cl.
CPC .............. *A61F 7/0085* (2013.01); *A61F 7/02* (2013.01); *A61F 7/03* (2013.01); *A61F 13/105* (2013.01); *A61F 17/00* (2013.01); *A61H 7/00* (2013.01); *A61H 33/04* (2013.01); *A63B 21/00189* (2013.01); *A63B 21/0414* (2013.01); *A63B 21/0552* (2013.01); *A63B 21/4033* (2015.10); *A63B 23/03508* (2013.01); *B65D 43/163* (2013.01); *G06Q 50/22* (2013.01); *G09B 19/003* (2013.01); *G09B 19/0038* (2013.01); *G09B 23/28* (2013.01); *A61F 2007/0036* (2013.01); *A61F 2007/0078* (2013.01); *A61F 2007/0242* (2013.01); *A61F 2007/108* (2013.01); *A61H 2033/047* (2013.01); *A61H 2201/0119* (2013.01); *A61H 2201/0157* (2013.01); *A61H 2201/0207* (2013.01); *A61H 2201/0214* (2013.01); *A61H 2201/0228* (2013.01); *A61H 2201/0257* (2013.01); *A61H 2201/1261* (2013.01); *A61H 2201/165* (2013.01); *A61H 2201/168* (2013.01); *A61H 2201/1635* (2013.01); *A61H 2201/5043* (2013.01); *A61H 2201/5048* (2013.01); *A61H 2201/5058* (2013.01); *A61H 2201/5064* (2013.01); *A61H 2201/5071* (2013.01); *A61H 2201/5097* (2013.01); *A61H 2205/065* (2013.01); *A61H 2205/067* (2013.01); *A63B 21/4039* (2015.10); *A63B 23/03533* (2013.01); *A63B 71/0622* (2013.01); *A63B 2071/063* (2013.01); *A63B 2210/50* (2013.01); *A63B 2220/806* (2013.01); *A63B 2225/64* (2013.01); *A63B 2225/66* (2013.01)

(58) Field of Classification Search
CPC ....... A61F 2007/0242; A61F 2007/108; A61H 7/00; A61H 33/04; A61H 2033/047; A61H 2201/0119; A61H 2201/0157; A61H 2201/0207; A61H 2201/0214; A61H 2201/0228; A61H 2201/0257; A61H 2201/1261; A61H 2201/1635; A61H 2201/165; A61H 2201/168; A61H 2201/5043; A61H 2201/5048; A61H 2201/5058; A61H 2201/5064; A61H 2201/5071; A61H 2201/5097; A61H 2205/065; A61H 2205/067; G06Q 50/22; B65D 43/163; G09B 19/003; G09B 19/0038; G09B 23/28; G06F 19/3418; G06F 19/3456; G06F 19/34812; G16H 20/30

See application file for complete search history.

(56) References Cited

U.S. PATENT DOCUMENTS

| | | | |
|---|---|---|---|
| 6,213,918 | B1 | 4/2001 | Rogers, Jr. |
| 6,707,380 | B2 * | 3/2004 | Maloney ............ G07C 9/00896 235/375 |
| 7,953,433 | B2 * | 5/2011 | Langlois ................ G08C 21/00 455/550.1 |
| 8,157,709 | B2 | 4/2012 | Wilkinson et al. |
| 8,754,769 | B2 | 6/2014 | Stein et al. |
| 9,125,798 | B2 | 9/2015 | Stein et al. |
| 9,358,183 | B2 | 6/2016 | Stein et al. |
| 10,071,023 | B2 | 9/2018 | Stein et al. |
| 2013/0143718 | A1 * | 6/2013 | Pani .................. A63B 21/4035 482/8 |
| 2015/0031511 | A1 | 1/2015 | Matthews |

\* cited by examiner

HAND THERAPY KIT WITH PRESENCE SENSORS

RELATED APPLICATIONS

This application is a continuation-in-part of U.S. application Ser. No. 16/016,098, titled "Hand Therapy Kit and Electronic Guide," filed on Jun. 22, 2018, which is a continuation-in-part of U.S. application Ser. No. 15/348,623, titled "Hand Therapy Kit," filed on Nov. 10, 2016, now U.S. Pat. No. 10,029,146, which is a continuation of U.S. application Ser. No. 14/640,943, titled "Hand Therapy Kit," filed on Mar. 6, 2015, now U.S. Pat. No. 9,616,287, which are incorporated herein by reference.

TECHNICAL FIELD

The present application is directed to systems for therapeutically treating the hand and/or upper extremity (e.g., forearm, elbow, and/or shoulder) of a patient. In particular, the present application is directed to a multi-part kit integrated into a case, housing or enclosure adapted for providing physical therapy for a hand in a home setting with little or no active participation by a professional therapist during its use including with a computer-driven guide for enhanced operation.

BACKGROUND

Currently, a patient that needs physical/occupational therapy for the hand needs to go to a professional office, such as a doctor's office or a physical therapist's office, to receive treatment. This can be a significant undertaking for a patient that needs to travel a long distance, take time away from work, and/or secure childcare so the patient can attend a physical therapy appointment at a professional office. This undertaking is compounded by the number of sessions the patient needs to attend, which can often repeat over multiple weeks or months.

Further, appointments at a professional office are expensive both to the patient and to the insurance provider. With increasing cost of healthcare premiums/deductibles, patients bear the burden of out of pocket expenses. Paying $30-50 co-pays per session—with treatment averaging 2 sessions a week for 6-8 weeks—is very expensive and cost prohibitive for most patients.

In addition, patients are often frustrated because many of the exercises that they perform with a professional physical therapist could be done at home at a more convenient time and without unnecessary travel. Strength and dexterity in the hand can be improved using simple portable tools (e.g., clothes pins, rubber bands, putty) with appropriate direction and methodology. A comprehensive kit which contains therapeutic objects for home-based therapy is needed to address the current need.

SUMMARY

The present disclosure is directed to a device and a kit for home-based physical therapy of the hand. The present devices and systems overcome many of the shortcomings of existing devices and systems for treating the hand. In an aspect, the present device can improve strength and/or range of motion of the hand including the fingers thereof. The device and kit include an elastic cord attached to a rigid surface at two or more contact points to define a gap for receiving a finger. A finger can be inserted in the gap and moved form a first position proximal to the rigid surface to a second position distal to the rigid surface for a therapeutic exercise. The kit can also include a therapeutic tracking glove and/or a pressure sensor ball.

An aspect of the invention is directed to a hand therapy kit comprising: a plurality of hand therapy modules; a housing that includes an upper lid and a lower lid, wherein said upper lid is removable from the lower lid to open said housing and said upper lid is engageable with the lower lid to close said housing, said upper and lower lids defining a plurality of receptacles to removably receive the hand therapy modules; a plurality of module presence sensors, each module presence sensor disposed in a respective receptacle and having a first state when a corresponding hand therapy module is disposed in the receptacle and a second state when the corresponding hand therapy module is removed from the receptacle; and a microprocessor disposed in the housing, the microprocessor in electrical communication with each module presence sensor to determine whether each module presence sensor is in the first state or in the second state.

In one or more embodiments, the microprocessor transmits module presence sensor data to a server through a communications interface disposed on or in the housing. In one or more embodiments, the communications interface includes a wired communications interface, a wireless communications interface, or a combination thereof. In one or more embodiments, the kit further comprises an alert module comprising a light source, a speaker, or a combination thereof, the alert module in electrical communication with the microprocessor to receive an alert command that activates at least one of the light source or the speaker.

In one or more embodiments, a first module presence sensor comprises a light sensor that receives a light emitted from a light source disposed in a first receptacle when the hand therapy module is removed from the first receptacle and that does not receive the light when the hand therapy module is disposed in the first receptacle. In one or more embodiments, a first module presence sensor comprises a load sensor, disposed on a bottom of a first receptacle, to sense a weight when the hand therapy module is disposed in the first receptacle and to not sense the weight when the hand therapy module is removed from the first receptacle. In one or more embodiments, the kit further comprises a first electrode disposed in a first receptacle and a second electrode disposed on an external surface of a first hand therapy module, the first and second electrodes in electrical contact when the first hand therapy module is disposed in the first receptacle and the first and second electrodes not in electrical contact when the first hand therapy module is removed from the first receptacle, and wherein a first module presence sensor comprises a voltage sensor, the voltage sensor sensing a first voltage in a circuit that includes the first and second electrodes when the first hand therapy module is disposed in the first receptacle, the voltage sensor sensing a second voltage in the circuit when the first hand therapy module is removed from the first receptacle.

In one or more embodiments, a first module presence sensor comprises a barcode reader disposed in a first receptacle and a barcode is disposed on an external surface of a first hand therapy module, the barcode reader reading the barcode when the first hand therapy module is disposed in the first receptacle, the barcode reader not reading the barcode when the first hand therapy module is removed from the first receptacle. In one or more embodiments, a first module presence sensor comprises an RFID reader disposed in a first receptacle and an RFID tag is disposed on or in a first hand therapy module, the RFID reader reading the RFID tag when the first hand therapy module is disposed in the first receptacle, the RFID reader not reading the RFID tag when the first hand therapy module is removed from the first receptacle. In one or more embodiments, the kit further comprises a memory operatively coupled to the microprocessor to store a status of each module presence sensor.

Another aspect of the invention is directed to a hand therapy kit comprising: a plurality of containers; a plurality of hand therapy modules, each hand therapy module disposed in a respective container; a plurality of container presence sensors, each container presence sensor disposed in a respective container and having a first state when a corresponding hand therapy module is disposed in the container and a second state when the corresponding hand therapy module is removed from the container; and a microprocessor in electrical communication with each container presence sensor to determine whether each container presence sensor is in the first state or in the second state.

In one or more embodiments, the microprocessor transmits container presence sensor data to a server through a communications interface disposed on or in the housing. In one or more embodiments, the communications interface includes a wired communications interface, a wireless communications interface, or a combination thereof. In one or more embodiments, the kit further comprises an alert module comprising a light source, a speaker, or a combination thereof, the alert module in electrical communication with the microprocessor to receive an alert command that activates at least one of the light source or the speaker.

In one or more embodiments, a first container presence sensor comprises a light sensor disposed that receives a light emitted from a light source when the hand therapy module is removed from the first receptacle and that does not receive the light when the hand therapy module is disposed in the first receptacle, the light sensor and the light source on opposite sides of the container. In one or more embodiments, a first module presence sensor comprises a load sensor, disposed on a bottom of a first container, to sense a weight when the hand therapy module is disposed in the first container and to not sense the weight when the hand therapy module is removed from the first container. In one or more embodiments, the kit further comprises a first electrode disposed in a first container and a second electrode disposed on an external surface of a first hand therapy module, the first and second electrodes in electrical contact when the first hand therapy module is disposed in the first container and the first and second electrodes not in electrical contact when the first hand therapy module is removed from the first container, and wherein a first container presence sensor comprises a voltage sensor, the voltage sensor sensing a first voltage in a circuit that includes the first and second electrodes when the first hand therapy module is disposed in the first container, the voltage sensor sensing a second voltage in the circuit when the first hand therapy module is removed from the first container.

In one or more embodiments, a first container presence sensor comprises a barcode reader disposed in a first container and a barcode is disposed on an external surface of a first hand therapy module, the barcode reader reading the barcode when the first hand therapy module is disposed in the first container, the barcode reader not reading the barcode when the first hand therapy module is removed from the first container.

In one or more embodiments, a first module presence sensor comprises an RFID reader disposed in a first container and an RFID tag is disposed on or in a first hand therapy module, the RFID reader reading the RFID tag when the first hand therapy module is disposed in the first container, the RFID reader not reading the RFID tag when the first hand therapy module is removed from the first container. In one or more embodiments, the kit further comprises comprising a memory operatively coupled to the microprocessor to store a status of each container presence sensor.

In one or more embodiments, the kit further comprises a housing that defines a plurality of receptacles, each container disposed in a corresponding receptacle. In one or more embodiments, the kit further comprises a plurality of lid sensors, each lid sensor in electrical communication with the microprocessor, wherein each container includes a lid removably disposed on a housing, and a respective lid sensor is disposed on each lid, each lid sensor having a first state when the lid is opened and a second state when the lid is closed.

Yet another aspect of the invention is directed to a computer-implemented method for remotely monitoring a usage of removable hand therapy modules, comprising: in a computer: receiving module presence sensor data that includes a state of each of a plurality of module presence sensors, each module presence sensor disposed in a corresponding receptacle defined in a housing of a kit, each module presence sensor having a first state when a corresponding hand therapy module is disposed in the corresponding receptacle and a second state when the corresponding hand therapy module is removed from the corresponding receptacle; analyzing the module presence sensor data to determine a measured usage frequency of each hand therapy module; comparing the measured usage frequency of each hand therapy module to a treatment plan, the treatment plan including a prescribed usage frequency for each hand therapy module; and generating a noncompliance alert when the measured usage frequency of at least one hand therapy module is lower than the prescribed usage frequency.

In one or more embodiments, each module presence sensor is disposed in a corresponding receptacle defined in a kit housing. In one or more embodiments, each module presence sensor is disposed in a container.

In one or more embodiments, the method further comprises sending an alert message to a third party, the alert message including the noncompliance alert. In one or more embodiments, the third party includes a physical therapist, an insurance agency, or both the physical therapist and the insurance agency.

In one or more embodiments, the method further comprises sending a warning command to the kit, the kit comprising a microprocessor and an alert module in electrical communication therewith, the warning command causing the microprocessor to activate the alert module, the alert module including a light source, a speaker, or both the light source and the speaker. In one or more embodiments, the method further comprises sending a warning message to a patient associated with the kit, the warning message indicating a detected variance from the treatment plan.

IN THE DRAWINGS

For a fuller understanding of the nature and advantages of the present concepts, reference is made to the following detailed description of preferred embodiments and in connection with the accompanying drawings, in which.

DETAILED DESCRIPTION

Figure 1:
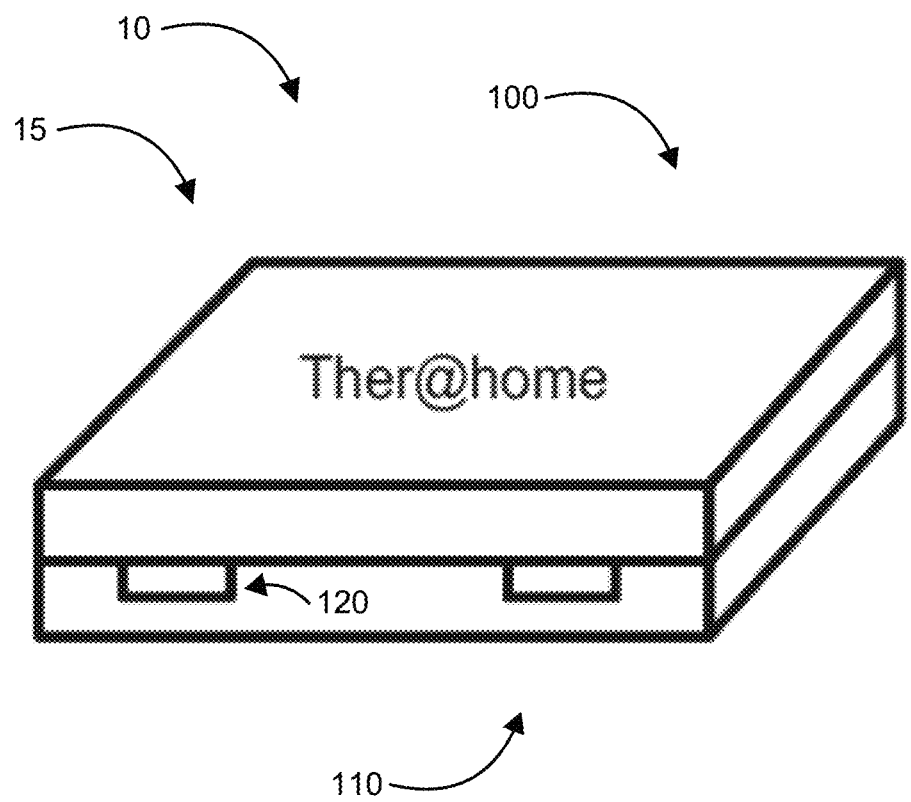
FIG. 1 illustrates a perspective view of a kit according to an embodiment.

A hand therapy kit includes a housing having a lid that is expandable from a folded position to an unfolded position to expose a working surface on an inside of the lid. An elastic cord is attached at two or more anchor points on the working surface to define at least one gap for receiving a finger. The finger can be therapeutically exercised by moving from a first position proximal to the working surface to a second position distal to the working surface. The hand therapy kit can also include removable hand therapy modules. There is no comprehensive self-guided "home-based kit" on the market that treats a patient's upper extremity ailments.

In another aspect, an apparatus for providing home-based physical therapy to a hand is disclosed. The apparatus includes an elastic cord attached to a rigid platform at two or more contact points. The contact points define a gap there between for receiving a finger. The finger can be therapeutically exercised by moving from a first position proximal to the rigid platform to a second position distal to the rigid platform.

The hand therapy kit and apparatus can be used by patients to provide physical therapy in a home environment. This provides a more convenient and cost-effective solution for the patient. By using the hand therapy kit and apparatus, the patient can improve strength, dexterity, and/or range of motion of his hand and fingers. Also, use of the kit can reduce healthcare costs and individual patient costs by allowing the user to participate in physical therapy at home with minimal to no involvement by medical personnel (e.g., doctors, physical therapists, etc.) and minimal to no use of medical offices.

The kit can include a camera and a processor for motion recognition. The motion recognition system can include instructions to compare the user's exercise techniques with model exercise techniques to provide feedback to the user. In addition or in the alternative, the kit can include equipment for video calls, such as a display, a processor, a video camera, and a network interface. The user can make video calls with a healthcare provider for instruction, monitoring of the user's progress, and/or health appointments. In addition or in the alternative, the video camera can record the user's exercises for therapists and doctors to use to treat the user and/or research purposes.

The kit can also include a therapeutic tracking glove and/or a pressure sensor ball. The tracking glove includes sensors to measure the range of motion of the user's hand, including the finger joints and wrist. The pressure sensor ball includes an inner spherical body disposed in a compressible ball. A plurality of radial force sensors are distributed across the external surface of the spherical body to measure any force that is applied to the corresponding external surface of the compressible ball to which the radial force sensors are aligned.

Data from the therapeutic tracking glove and/or a pressure sensor ball can be sent via a wired or a wireless communication interface to an external device, such as a user's mobile device. The user's mobile device can include an application or app that can process and analyze the received data and to present the data to the user to track his/her progress. The application or app can also allow the user to send the data, in raw or modified form, to a third party such as his/her physical therapist. Therefore, the kit can include in some embodiments a system or sub-system for data collection and transmission, e.g., wired or wirelessly, to exchange or provide information, e.g., to and/or from a separate module or computing system or network-connected server, which in turn may be coupled to or include a data processor, memory device or database, and may be adapted to execute machine readable instructions. This data communication can be facilitated by software and hardware and using special or general data communication protocols. Connection may be established with connected or networked devices, including mobile communication devices, smart phones, computer systems, gaming consoles and the like.

In some aspects, the data connectivity features may be enabled and used through hardware and/or software user interfaces, e.g., on a user's mobile device running a local or web-based application. The mechanical exercise modalities will contain sensory input components which will be able to collect and transmit the data. The nature of the data will be various measurements and progress trackers analogous to the measurements taken by a certified hand or occupational therapist. The application itself can utilize various different technologies including but not limited to digital motion sensor capabilities and cluster recognition algorithms for injury measurements (using the device's camera), audio commands from both the app and from the user, video and audio calling interfaces for one on one conversations with the therapist, and comprehensive tutorial videos.

Additionally, the application can include a community-based comparator with a point system to incentivize progress checkpoints for therapy. It can also incorporate FAQs and forums for patients to talk with each other and with professionals other than their therapist. The present system and method can allow an effective and comfortable vehicle for hand therapy inside one's own home without the need to travel to a practitioner's location, seek parking, navigate unfamiliar facilities (especially if the patient is infirm or disabled), and without sacrificing the abilities of the physician and therapist to track progress and adapt treatment strategies.

In order to make the integration with this mobile/web application easier and more quantitative, the present invention may include a plurality of (e.g., two) sensory input devices for measurement of various hand, finger, and wrist quantities. One of these comes in the form of a glove that houses sensors necessary to measure movements in a comprehensive and accurate manner. The other is a grip and/or pinch strength measurement device utilizing radial sensors housed in a spherical or alternately shaped containment. Both can transmit wireless/wired data as discussed above, and may be coupled to a communication and processing circuit including a virtual reality (VR) system as appropriate.

In an embodiment, a patient may be provided with a wearable headset coupled to a VR interface presenting visual information to the patient. The patient could be presented through the VR with imagery in the visor of the headset, the imagery presenting for example a scene with the patient interacting virtually with a professional trainer, and the patient can see an image or representation in the VR display representing the patient's hand as well. This virtual hand tracking process may take inputs from one or more sensors, signals such as those described herein. For example, sensors measuring force, position, relative extension, speed, and other physical parameters can be used to acquire information to guide the therapy. The system generates information to create the virtual representation of the patient's hand for display in the VR headset. It should be appreciated that such data and imagery can be sent to a variety of processor based components of a therapy system, and stored for the patient's records in a memory unit, or otherwise shared with human or artificial therapists. Instructions to the patient and indications of success or necessary therapy steps can be generated and displayed visually or audibly through the VR interface.

In some embodiments, the kit includes a plurality of presence sensors that detect when each hand therapy module is present or absent from the kit, which can indicate when the patient is performing therapeutic exercises with the corresponding hand therapy module. The presence sensors can be disposed in receptacles, defined in the kit housing, that removably receive the hand therapy modules. In addition or in the alternative, the presence sensors can be disposed in containers that removably receive the hand therapy modules. The containers can be disposed in the receptacles in some embodiments. A microprocessor in the kit can send presence sensor data, via a wired or a wireless communication interface, to a remote server for data collection and analysis. The remote server can determine a measured usage frequency of each hand therapy module and compare the measure usage frequency with a prescribed usage frequency that can be included in a treatment plan (e.g., provided by a physical therapist). The remote server can generate warnings, alerts, and/or notifications when noncompliance with the treatment plan is detected.

FIG. 1 illustrates a perspective view of a kit 10 according to an embodiment. The kit 10 includes various components for therapeutic treatment of the hand as described herein. The kit 10 has an upper lid 100 and a lower lid 110. The upper lid 100 and the lower lid 110 can be connected by a hinge or similar mechanism. Alternatively, the upper lid 100 and lower lid 110 can be disconnected such that the upper lid 100 can be separated from the lower lid 110, for example to use as a work surface as described below. The upper lid 100 and lower lid 110 can be secured shut with an optional latch 120.

Figure 2:
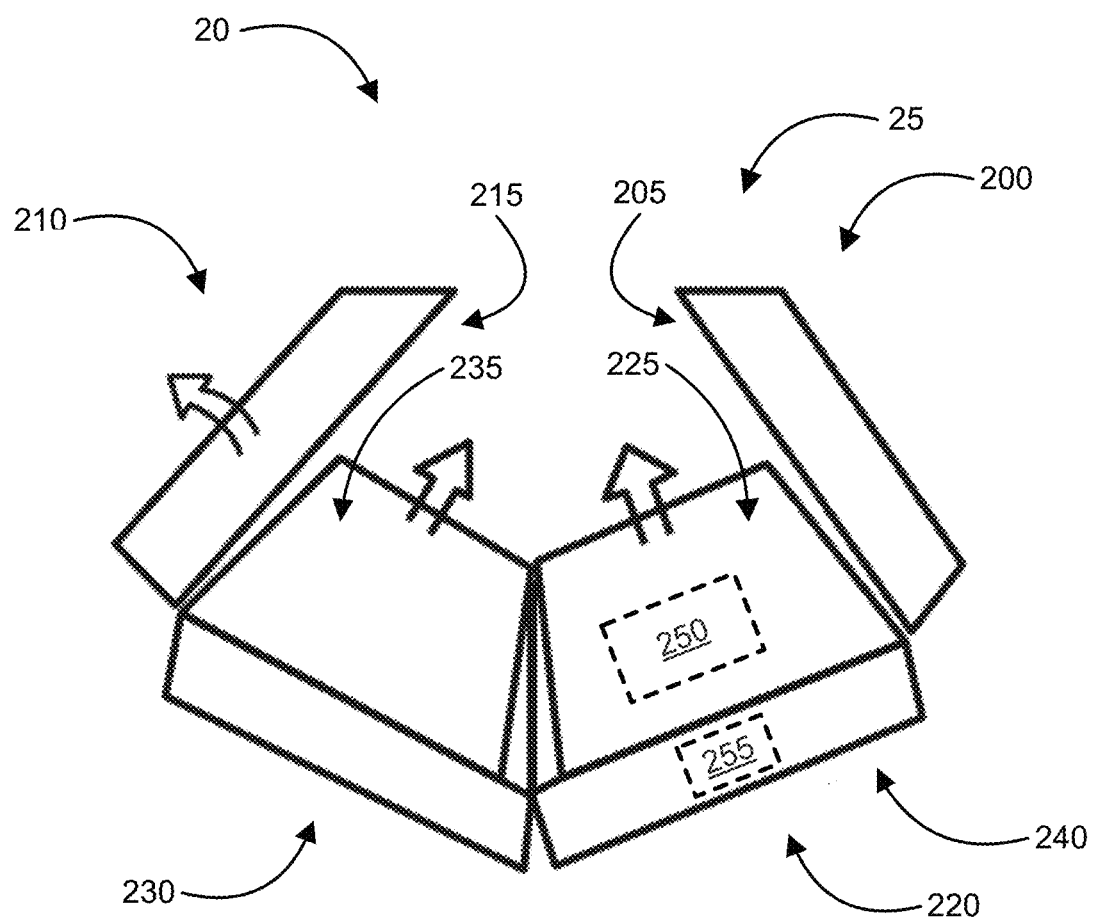
FIG. 2 illustrates a perspective view of a kit according to an embodiment.

FIG. 2 illustrates a perspective view of a kit 20 according to an embodiment. The kit 20 includes an upper lid 200 and a lower lid 210 as previously discussed. The upper lid 200 and lower lid 210 fold out laterally (e.g., in the direction of the arrows illustrated in FIG. 2) to expose secondary lid portions 220, 230, which include working surfaces 225, 235, respectively. The working surfaces 225 and/or 235 can include one or more devices, modules, and/or equipment for therapeutically treating the hand. In some embodiments, a lower surface 205 of the upper lid 200 and/or a lower surface 215 of the lower lid 210 include one or more devices, modules, and/or equipment for therapeutically treating the hand. In addition or in the alternative, the lower surface 205 of the upper lid 200 and/or the lower surface 215 of the lower lid 210 includes a working surface as described above. The working surfaces 225 and/or 235 can include a cavity to receive one or more modules.

In some embodiments, an optional heating element 250 is integrated into the upper lid 200 and/or lower lid 210, for example on one of the working surfaces 225, 235 or on one of the lower surfaces 205, 215. The element 250 can be used to warm paraffin wax (e.g., from the paraffin wax module 530C described below). The heating element 250 can be powered by a battery stored in the kit 20 or by external AC power provided through an electric cord 255, which can be integrated into the kit 20. In an embodiment, the housing or case of the kit can include an integrated AC power plug or connector so that the kit can accept an ordinary AC power extension cord to provide heating or other power to the units within the kit, e.g., as described below. For example, the electric cord 255 can pass through the inside of the kit 20 and out through a sidewall 240 of the kit 20. The electric cord 255 can be retractable so that it can be stored inside the kit 20. In some embodiments, the heating element 250 is disposed on a surface below the working surface 225, 235 in which case the working surface 225, 235 is removable so that a user can access the heating element 250.

Figure 3:
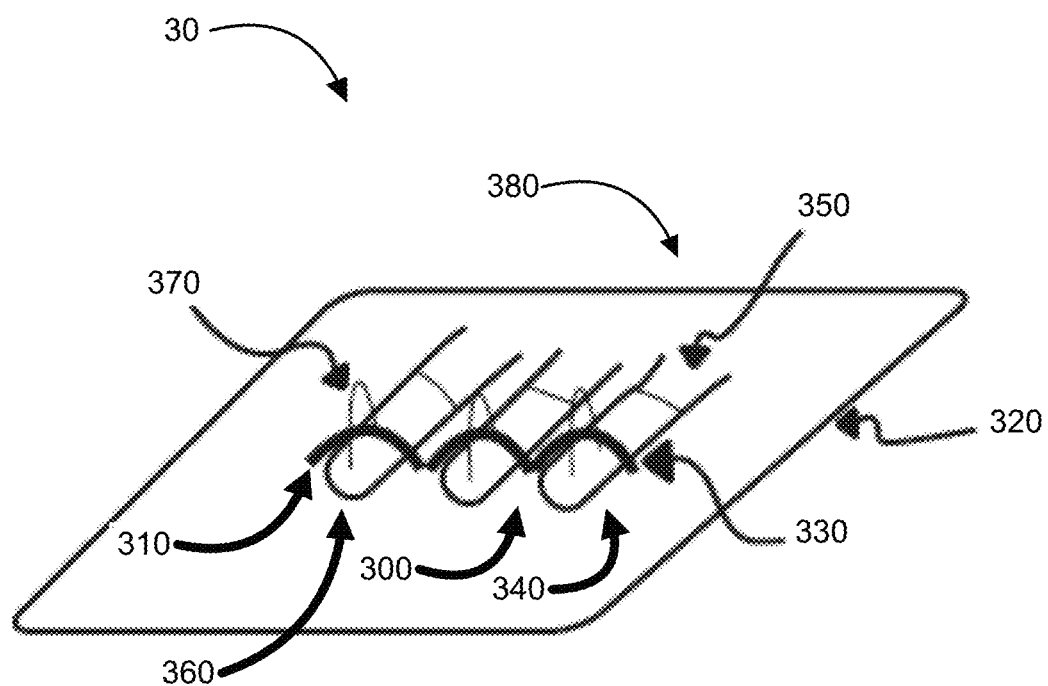
FIG. 3 illustrates a perspective view of an apparatus for therapeutically treating the hand according to an embodiment.

FIG. 3 illustrates a perspective view of an apparatus 30 for therapeutically treating the hand according to an embodiment. The apparatus 30 includes one or more elastic pulleys 300. The pulleys 300 are formed from an elastic cord 310 which can be made out of a flexible and/or stretchable material such as rubber, a rubber band, a bungee cord, a similar material, or combination thereof. The cord 310 is attached to a generally planar surface 320 of a rigid platform 380 at anchor points 330, which forms a gap 340 between adjacent anchor points 330. The gap 340 is generally sized to receive a finger 350. In some embodiments, the cord 310 consists of multiple discrete segments that extend between adjacent anchor points 330 to receive multiple fingers 350.

In operation, a patient inserts one or more fingers 350 in respective gaps 340. The finger(s) 350 are inserted so that the finger pad(s) 360 are exposed while the finger nail(s) (not shown) are adjacent to the surface 320. The patient bends the finger(s) 350 away from the surface 320 generally in a direction 370 (from a proximal to a distal position). As the patient bends the finger(s) 350, the elastic cord 310 provides a positive resistance for exercising and/or strengthening the finger(s) 350. In an aspect, the cord (or cords if it is made of several individual loops) can have a textured and/or heated surface to enhance the therapeutic action of the cords.

In some embodiments, the surface 320 and/or rigid platform 380 is formed of wood, plastic, cardboard, or similar material that is generally inflexible so that the surface 320 and/or rigid platform 380 does not deform during use of the pulleys 300. In some embodiments, the pulleys 300 are formed from two or more elastic cords 310A, 310B, 310N. Each elastic cord 310A, 310B, 310N can have the same or different resistance and can be formed from the same or different materials. The pulleys 300 can be disposed as a component and/or module of a hand therapy kit as described herein. Alternatively, the pulleys 300 can be integrated onto a working surface of a kit, as described above.

Figure 4:
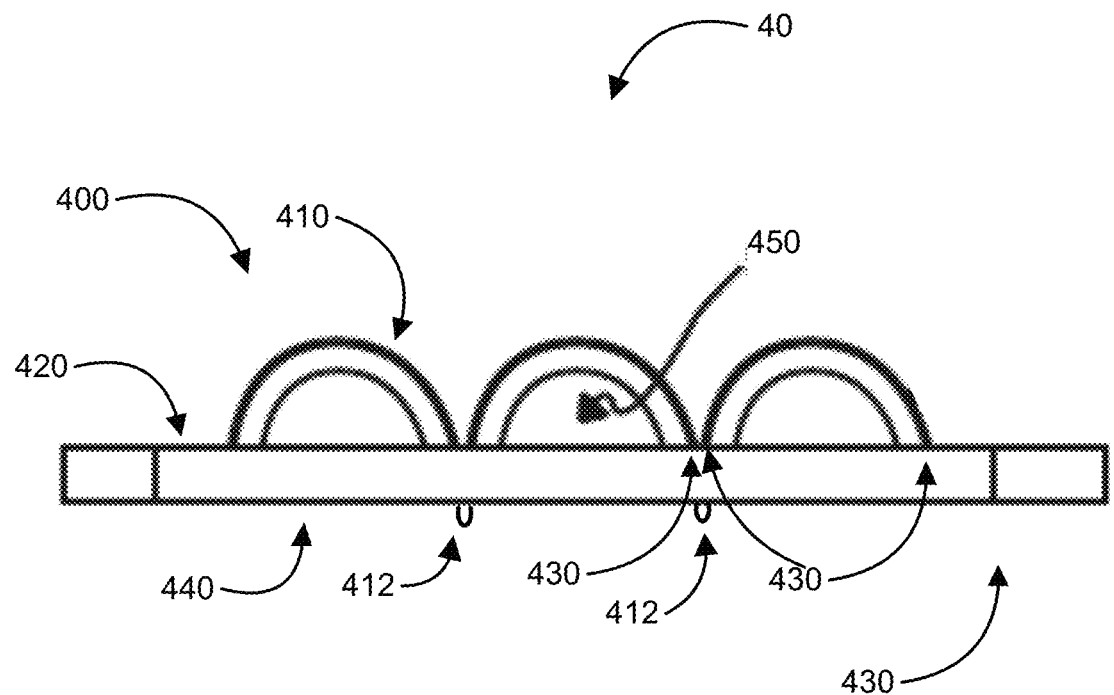
FIG. 4 illustrates a side view of an apparatus for therapeutically treating the hand, which generally corresponds to the apparatus illustrated in FIG. 3.

FIG. 4 illustrates a side view of an apparatus 40, which generally corresponds to the apparatus 30 described above. The apparatus 40 includes one or more elastic pulleys 400 formed of an elastic cord 410, which are secured to a block 440 at anchor points 430. In operation, a user inserts his fingertip(s) 450 under the elastic cord 410, such that the fingertip(s) 450 face towards the cord 410 and away from a surface 420 of the block 440. As discussed above, the surface 420 and the block 440 may be substantially inflexible and can be an independent component of a hand therapy kit or integrated onto a working surface of a kit.

In some embodiments, elastic cord 410 can be a single elastic cord that extends through each anchor point 430. The single elastic cord can pass through at least a portion of the block 440 to form each anchor point 430. For example, when the single elastic cord pass through to the underside of block 440, a portion 412 of the single elastic cord can be visible. Alternatively, elastic cord 410 can include multiple elastic cords, each elastic cord attached at two anchor points 430 to function as a pulley 400.

Figure 5:
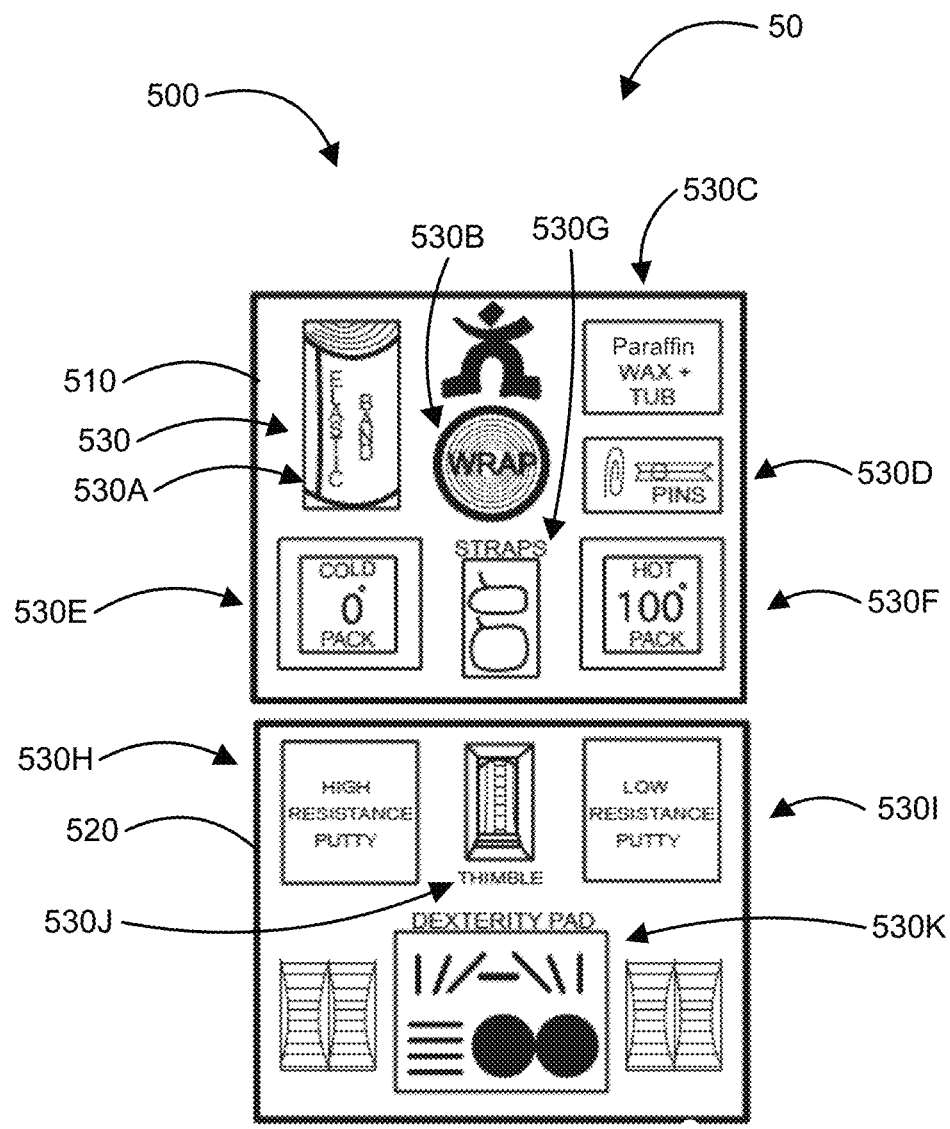
FIG. 5 illustrates a plan view of a kit according to an embodiment.

FIG. 5 illustrates a plan view of a kit 50 according to an embodiment. The kit 50 includes a plurality of hand therapy modules and components that are integrated into a housing, case or enclosure which is portable, cost-efficient and suited for the present purpose. While the kit may include some elements known in the art, several of the elements described herein are not. In addition, those skilled in the art would appreciate that other elements and modules can be integrated into kit 50 as well.

The kit 50 includes a housing 500 having an upper lid 510 and a lower lid 520 as generally described above. One or more hand therapy modules 530 for providing home-based therapeutic treatment for the hand are disposed in the kit 50. As illustrated, the modules 530 include an elastic band module 530A, a wrap module 530B, a paraffin wax module 530C, a clothespin module 530D, a cold pack module 530E, a hot pack module 530F, a strap module 530G, a high-resistance putty module 530H, a low-resistance putty module 530I, a thimble module 530J, and a dexterity pad module 530K. Greater or fewer modules 530 can be disposed in the kit 50. In some embodiments, the modules 530 are removable and/or interchangeable.

The elastic band module 530A includes multiple elastic bands having different sizes, shapes, and/or elasticities and can be formed out of rubber (natural or synthetic), bungee cord, or similar material. The elastic band module 530A can be used by a patient to exercise the hand (or various portions of the hand such as one or more fingers, etc.) at different resistances. For example, a patient can place an elastic band over a clenched first for exercising the hand by opening and closing the first against a resistive force provided by the elastic band. Such exercise can increase intrinsic and/or extrinsic muscle strength as well as dexterity. Intrinsic muscles include those that originate and insert within the hand; extrinsic muscles have an origin outside of the hand (e.g., the forearm). The kit 50 and/or elastic band module 530A can include instructions for using the elastic bands. In some embodiments, the elastic bands are color coded by resistivity (e.g., darker-colored bands are more resistive and lighter-colored bands are less resistive).

The wrap module 530B includes an elastic bandage that can be self-adhering in some embodiments. The elastic bandage can be formed out of a stretchable and/or flexible material. In operation, a patient can wrap the elastic bandage around one or more fingers, for example in a distal (towards fingertip) to proximal (towards knuckle) direction, to reduce swelling and/or to guide edema. Such a wrapped elastic bandage can also promote lymphatic drainage. The kit 50 and/or wrap module 530B can include instructions for using the elastic bandage.

The paraffin wax module 530C includes a source of paraffin wax (e.g., a tub) and a bath unit, which includes a heater to heat and melt the paraffin wax. In some embodiments, the bath unit can be designed to heat the paraffin wax to between about 125° F. and about 135° F. In operation, a patient can place her hand (or portion thereof or other extremity) in the bath unit, which contains heated and melted paraffin wax. The heated paraffin wax warms the tissue in the hand/extremity to make it more supple, elastic, and/or flexible before and/or during exercises. Pre-treatment of the hand in the paraffin wax bath can improve pain and range of motion during exercises.

In addition or in the alternative, the paraffin wax module 530C includes a paraffin glove, which can be heated (e.g., in the microwave) and worn by a patient. Such a glove can warm the entire hand at once not only before exercise/therapy but also during exercise/therapy. The kit 50 and/or paraffin wax module 530C can include instructions for using the paraffin wax, bath unit, and/or paraffin glove. In some embodiments, the glove includes a material that is exothermic with stretch to provide warmth during use. The glove can be reusable or microwaveable or washable.

Also, a compression glove could be provided as part of the kit and that can serve to reduce swelling. Such a glove may be a one-size-fits-most and can have an elastic or stretchable material to stretch over hands of various sizes.

A glove may be employed in some embodiments that is designed and arranged to fit around the entirety of a patient's hand, fingers, and to extend over a certain area of the wrist. A first set of sensors therein may be longitudinal in design and run the length of each finger on the inner hand. These can meet at a central location either in the center of the palm, outside the back of the hand, or the base of the hand near the wrist. The glove sensors may comprise a few distinct components as described herein.

For example, a first set of components of the glove system may be fixed parts on the inside of the hand. Similar to how a nerve runs through a tunnel, there would be fixed guided pathways running up the length of each finger.

In some aspects, one or more or every joint of the finger may comprise a hinge so that the pathway could bend without restricting the finger. These hinges would have a mechanical component like a dial or tick that shift position as that specific joint was flexed or extended. This would function as a goniometer. The goniometer could measure range of motion, ranging from 0 degrees to 90 degrees at the distal interphalangeal joint, 0 to 100 degrees at the proximal interphalangeal joint, and 0 to 100 degrees at the metacarpophalangeal joint. At the wrist level, the sensors could detect range of motion from 90 degrees of dorsi flexion, or wrist extension to 90 degrees of palmar flexion, or wrist flexion. The component's position would indicate an angle or a particular type of finger movement. The data received from these sensors would be transmitted to a recording device, either through wireless or wired means. This data would then be stored and organized using an algorithm encoded in a sequence of machine-readable program instructions executed on a processing circuit that categorizes the information. This information could then be referred back to or communicated to the physician or therapist, in order to monitor progress and help patients achieve targets or goals. This information would also enable better patient compliance as it would serve as a direct feedback of progress in various parameters.

In some examples, to transfer the mechanical inputs into electrical outputs for data transfer and analysis, the system comprises small wires running within the elastic bands. This way the current could be changed by hinge movement or overall extension, and thus, there would also be some electrical data to interpret.

A second set of glove sensors are longitudinal in design and run the length of the back of the hand and extend over the wrist. Similar to the sensors running along the palmar aspect of the hand, the dorsal sided sensors can be used in concert to fine tune the measurements, as they would be the supplement of the palmar sensor measurements.

Yet a third set of glove sensors could be located within the interior of the glove on the inside of the hand which can relay thermal output.

In the figure shown, the clothespin module 530D includes one or more clothespins and optionally a string, fabric, or other object for attaching clothespins thereto. In operation, a patient uses her fingers to open the clothespins and attach them to the string, fabric, or other object. Such an exercise can improve the strength of the patient's fingers (e.g., the "pinch" strength) as well as her dexterity. The kit 50 and/or clothespin module 530D can include instructions for using the clothespins.

The cold pack module 530E includes one or more cold packs, which can come in a variety of forms such as a flexible cold pack (e.g., containing a gel or beads), a rigid cold pack, etc. The cold pack can be cooled by placing it in a refrigerator or freezer unit. Alternatively, the cold pack can be cooled by inserting ice and/or a cool liquid in an internal cavity defined by the cold pack. In operation, a patient places the cold pack on a body part (e.g., the hand) before or after exercising the body part to reduce swelling and/or reduce pain. The kit 50 and/or cold pack module 530E can include instructions for using the cold packs. The cold pack can be reusable.

The hot pack module 530F includes one or more hot packs, which can come in a variety of forms such as a flexible hot pack (e.g., containing a gel or beads), a rigid hot pack, etc. The hot pack can be warmed by heating it in a microwave or with an electric current. Alternatively, the hot pack can be warmed by pouring a warm liquid (e.g., hot water) into an internal cavity defined by the hot pack. In operation, a patient places the hot pack on a body part (e.g., the hand) before or after exercising the body part to improve flexibility and/or range of motion. The kit 50 and/or hot pack module 530F can include instructions for using the hot packs.

In some embodiments, the cold pack module 530E and the hot pack module 530F are integrated into a single module. For example, the integrated hot/cold pack module can include a thermal pack with a gel that stays hot when heated (e.g., in the microwave) and that stays cool when cooled (e.g., in the freezer). Alternatively, the hot/cold pack module can be a smart material that produces heat when stretched and cools when compressed.

The strap module 530G includes a strap made out of a fabric, such as a nylon or polyester. In operation, a patient can wrap the strap around an object and exercise her hand muscles (e.g., the grip muscles) by pulling on the strap. In some embodiments, the patient can secure the strap in a door jam. In addition or in the alternative, a patient can pull opposing ends of the strap to exercise both hands at the same time. The kit 50 and/or strap module 530G can include instructions for using the straps. In an aspect, a multi-strap finger exercise module allows for exercising of one or more fingers, for example simultaneously. The straps may be elastic or spring loaded from beneath, or may be otherwise mechanically resistive to elongation when under tensile stress. Strength and dexterity of the fingers and of associated hand muscles and tissues is achievable through a regimen of exercise using the elastic strap module 530G.

The high-resistance putty module 530H and low-resistance putty module 530I include various containers or pellets of therapeutic putty having various resistances. The putty can be formed out of silicone, rubber, silicone rubber, or other synthetic and/or natural materials with similar properties. In some embodiments, the resistance of the putty can vary as the user stretches or compresses the putty. In operation, a patient can squeeze the putty in her hand to improve grip and overall hand strength. A patient can also squeeze the putty between her fingers to improve pinch strength and/or to exercise weaker fingers in isolation. A patient can also pull the putty apart using two hands to exercise both hands simultaneously. In some embodiments, the patient can begin physical therapy using the low-resistance putty module 530I and, after gaining strength, the patient can transition to using the high-resistance putty module 530H. The kit 50, the high-resistance putty module 530H, and/or the low-resistance putty module 530I can include instructions for using the putty.

Figure 6:
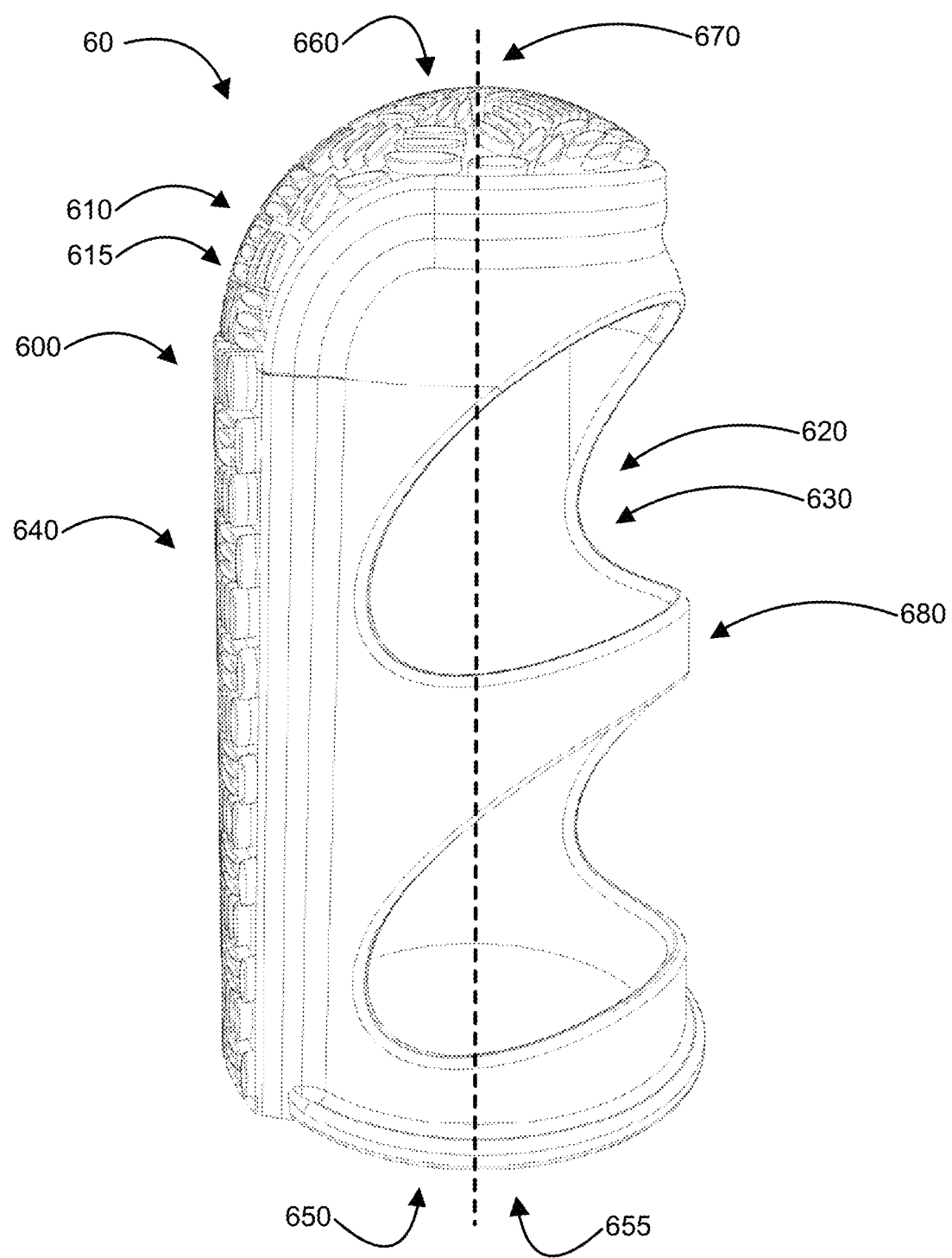
FIG. 6 illustrates a perspective view of a thimble for treating a scar according to an embodiment.

The thimble module 530J includes one or more thimbles for decreasing sensitivity of scars throughout the body and/or for improving fingertip hypersensitivity. FIG. 6 is a perspective view of a thimble 60 that can be included in the thimble module 530J. The thimble 60 has a textured exterior region 610, which can be used for rubbing scar tissue. In addition, the thimble can include an interior cavity 620 lined with silicone. In some embodiments, the thimble module includes one or more thimbles as described in U.S. patent application Ser. No. 14/474,751, entitled "Apparatus for Reducing the Appearance and Effects of Scars," which is hereby incorporated herein by reference and assigned to the same assignee as the present application. A patient can wear the thimble 60 (with the fingertip touching the interior cavity 620) to decrease the sensitivity of a fingertip, which can become hypersensitive due to scarring. In addition, a patient can wear the thimble 60 on a finger to help soften a scar, to improve cosmesis, and/or to decrease pain.

In general, the thimble includes a body 600 having an interior surface 630 and an exterior surface 640. The exterior surface 630 includes features 615 that provide one or more textured regions 610 that a patient can rub against the affected area. The textured regions 610 can have a varying coarseness or roughness. The features 615 can include raised bumps, grooves, or other shapes that have a coarseness appropriate for the skin condition and/or the treatment regimen. The textured regions 610 can have features 615 arranged in various patterns, which can have variations within the pattern such as the distance between each feature and adjacent features, the arrangement of the features (e.g., in linear columns and rows or an offset between adjacent columns and/or rows), and/or the hardness or flexibility of the material that creates the features. These variables, described above, can be the same or different across the textured region 610.

The body 600 has a cavity 620 to receive one or more fingers. A proximal end 650 of the body 600 defines an aperture 655 to allow a finger to penetrate the cavity 620. The interior surface 630 of the distal end 660 of the body 600 is adapted to conform to the tip of one or more fingers. Thus, a patient can mount the apparatus 60 on a finger by inserting the finger(s) through the proximal end 650 of the body 600 and through the cavity 620 to the distal end 660 of the body 600. The patient can then bend her finger with her finger inserted in the apparatus 60 to provide resistive movement to strengthen the finger joint(s).

The cavity 620 can be cylindrical and can have a central axis 670 extending from the proximal end 650 to the distal end 660 of the body 600. A support member 680 can be disposed on the body 600 to enhance the mechanical strength of the device 60. The support member 680 can be disposed in an orientation orthogonal to the central axis 670.

As discussed above, the thimble device has one or more textured regions 610. For example, a first textured region can have a coarseness appropriate for a first portion of a treatment regimen and a second textured region can have a coarseness appropriate for a second portion of the treatment regimen. The second textured region can have a greater or lower coarseness or roughness than the first textured region. The first and second textured regions can have other variations including the pattern of the features within each textured region, the distance between each feature, the arrangement of the features (e.g., in linear columns and rows or an offset between adjacent columns and/or rows), and/or the hardness or flexibility of the material that creates the features.

In some embodiments, two or more thimbles are included in the thimble module 570J. A first thimble, similar to the thimbles described above, has at least one textured region having a first coarseness appropriate for a first portion of a treatment regimen. A second thimble, also similar to the thimbles described above, has at least one textured region having a second coarseness appropriate for a second portion of the treatment regimen. The thimble module 570J can include additional devices having varying coarseness, which can be used for other portions of the treatment regimen.

Figure 26:
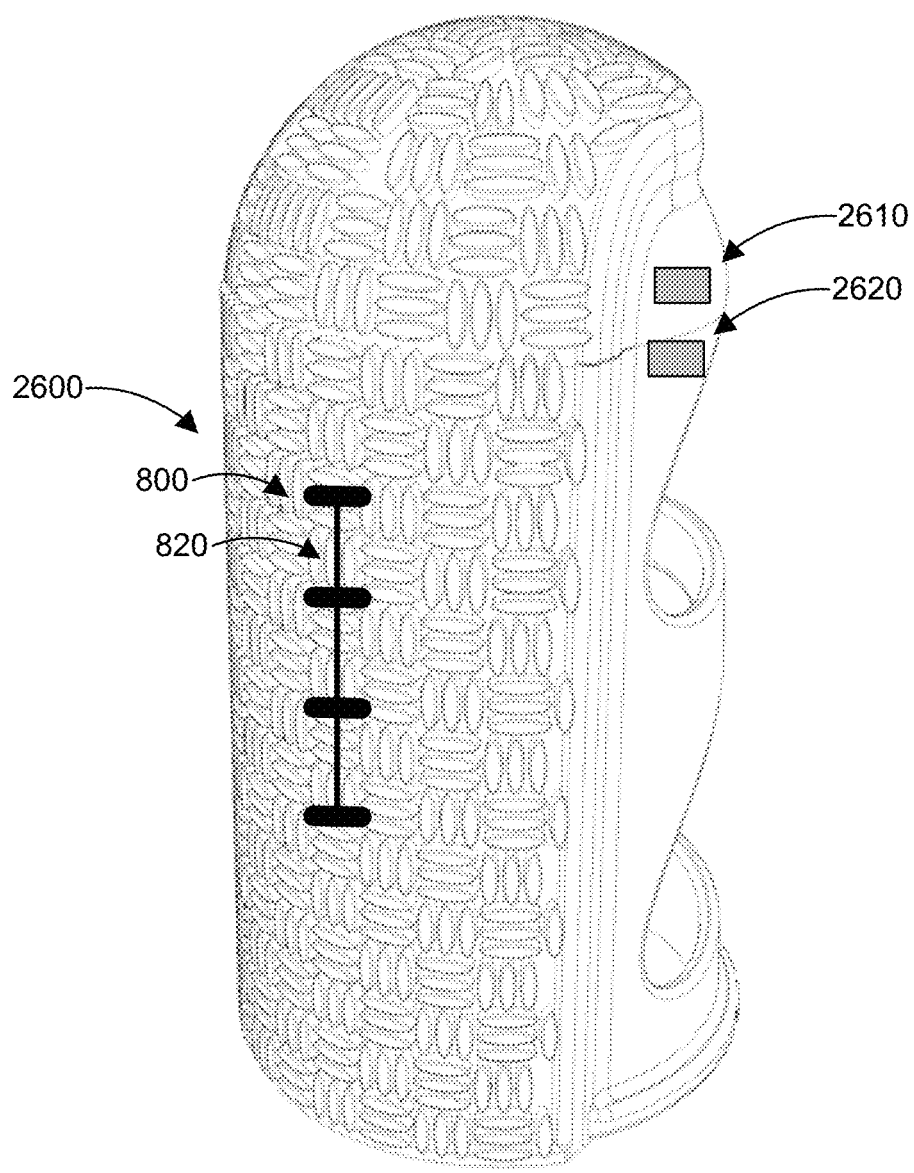
FIG. 26 illustrates a perspective view of a thimble that includes rotational-position sensors, according to one or more embodiments.

In some embodiments, the thimble apparatus 60 includes one or more rotational-position sensors 800 that are mechanically coupled to wires or rods 820, as illustrated in FIG. 26. The rotational-position sensors 800 and rods 820 can comprise a rotational sensor apparatus 2600 that can be the same as or different than rotational sensor apparatus 90, discussed below. The rotational-position sensors 800 are disposed on or in the thimble apparatus 60 to detect its deflection and/or rotation during use (e.g., when a user bends his/her finger with his/her finger inserted in the apparatus 60). Thus, the rotational-position apparatus 2600 can detect when the thimble apparatus 60 is being used, the number of therapeutic exercise repetitions performed, and the finger's range of motion.

In addition or in the alternative, a temperature sensor 2610 and/or an accelerometer 2620 can be disposed in the thimble apparatus 60. The temperature sensor 2610 can sense an increase in temperature when a user's finger is inserted in the thimble apparatus 60 and a decrease in temperature when the user's fingers is removed from the thimble apparatus. Thus, the temperature sensor 2610 can detect when and how often the thimble is being used. The accelerometer 2620 can sense a change in motion (e.g., acceleration) of the thimble apparatus 60, for example when the thimble apparatus 60 is removed from the kit and/or when the thimble apparatus 60 is bent during therapeutic exercise.

The rotational-position sensors 800, the temperature sensor 2610, and/or the accelerometer 2620 can include or can be operatively coupled to a microprocessor and a communications device, such as a wired or a wireless communication device, to transmit respective data directly or indirectly to one or more servers. For example, the wired or wireless communications device can transmit data to the kit, a mobile phone, a computer, a tablet, or other device, which can then directly or indirectly transmit the data to the server(s).

Overall, the kit can include contours in its internal walls or working platform structures. For example, outwardly concave contours, hemispherical or similar extrusions can be textured and provide a touching and grasping action for certain therapeutic exercises.

In addition, the thimble module 570J can include a therapeutic cream, which can be used to treat a dermatological condition (e.g., scars, burns, keloids, skin blemishes, incisions, lacerations, abrasions, and/or stretch marks) together or in combination with the thimble described above. The cream can include one, some, or all of the ingredients in Table 1. It is noted that the weight percentages provided in Table 1 are examples and are not intended to be exhaustive. For example, the cream can include plus or minus 1%, 2.5%, 5%, 10%, or 15% of the weight percentage of any ingredient listed in Table 1. The cream can have a pH of about 5.9 (at 25° C.) plus or minus 1%, 2.5%, 5%, 10%, or 15% and it can have a viscosity of about 200,000 cps plus or minus 1%, 2.5%, 5%, 10%, or 15%.

TABLE 1

| Ingredient | Weight Percent | Function |
|---|---|---|
| Deionized water | 57.30 | Vehicle |
| Glycerin | 5.00 | Humectant |
| Propanediol | 2.00 | Solvent moisturizer |
| SabiWhite ™ (tetrahydrocurcumin 95%) (Sabinsa Corporation) | 0.20 | Skin lightener, antioxidant |
| *Aloe barbedensis* | 2.00 | Anti-inflammatory |
| Carbopol ® Ultrez 10 (carbomer) (Lubrizol Corporation) | 0.80 | Rheology, viscosity |
| Vital ET ™ (disodiumLauriminodipropionate tocopheryl phosphates) | 2.50 | VE phosphate non-steroidal anti-inflammatory, source |

TABLE 1-continued

| Ingredient | Weight Percent | Function |
|---|---|---|
| (Ashland Inc.) | | of Vitamin E |
| Allantoin | 0.50 | Stimulates new tissue growth, wound healing |
| Muira puama (*ptychopetalum olacoides*) bark/root extract (and) glycerin (and) water) | 0.50 | Increase blood flow, antiseptic, antibacterial |
| Cutina ® GMS V (glyceryl stearate) (BASF Corporation) | 1.00 | Emulsifier |
| Phenoxyl T (cetearyl alcohol (and) ceteareth-20) | 2.00 | Emulsifier |
| Alpha-bisabolol | 0.20 | Non-steroidal anti-inflammatory |
| Cocoa butter (*theobroma cacao* seed butter) | 2.00 | Reduces degeneration of skin cells and restores skin flexibility |
| Cremelin ® PURA (vegetable oils) (CREMER OLEO GmbH & Co. KG) | 1.00 | Natural petrolatum |
| Almond oil (*prunus amygdalus dulcis*) | 1.00 | Emollient |
| Olive oil (*olea europaea*) | 1.00 | Soothing, promotes oil spreading and skin smoothness |
| Jojoba oil (*simmondsia chinesis*) | 8.00 | Wax esters for antioxidant, moisture emollient, improves skin elasticity |
| Dow Corning ® 200, 100 cSt (dimethicone) (Dow Corning Corporation) | 0.50 | Silicone spreading |
| Freshcolat ® MGA (menthone glycerine acetal) (Symrise AG) | 1.00 | Skin coolant and refreshant |
| Triethanolamine 99% | 0.60 | pH adjustment |
| Escalol ® 557 Octinoxate (Ashland Inc.) | 1.00 | UV absorber |
| Germaben ® II (propylene glycol (and) diazolidinyl urea (and) methylparaben (and) propylparaben) (Sutton Laboratories) | 1.00 | Preservative |
| Phytotal ™ AI PS (glycerin, aqua, butylene glycol, *euphrasia officinalis* extract, *melissa officinalis* extract, *magnolia biondii* extract, lecithin) (Croda International PLC) | 2.30 | Reduces visible and physical signs of irritation |
| SymSitive ® 1609 (pentylene glycol, 4-t-butylcyclohexanol) (Symrise AG) | 3.00 | Reduces neuropathic pain (e.g., stinging and burning) |
| Cucumber phytobasic in glycerine (*cucumis sativa* extract) | 2.30 | Astringent/skin tightening |
| Pro-Lipo ™ Neo (propanediol (and) lecithin) (Unipex Group Inc.) | 1.30 | Pro-liposome encapsulation skin penetrant; increases skin penetration and bioavailability of entrapped hydrophilic and/or lipophilic active ingredients for better and faster results |

The cream can be infused or stored in a silicone (or similar) elastomer sheet or pad, which can be available in various sizes to use as a dressing over a surgical or traumatic scar. The cream can be located in a recessed compartment within the elastomer sheet or pad. The elastomer sheet or pad can be stored prior to clinical application by using an impermeable or semipermeable peel away covering. For example, the elastomer sheet or pad can be sized and shaped to fit over a caesarian section scar. The sheet or pad can be applied over the entire length of the scar for several weeks following the caesarian section procedure, allowing the scar (and the patient) to benefit from the cream contained in the sheet or pad. Additionally, the sheet or pad can retain moisture, which can soften a scar and protect the skin from post-surgical hypersensitivity.

When used with the thimble, the cream can flow through interstices or channels of the textured regions. For example, the cream can flow through interstices or channels of the first textured region at a first rate and can flow through interstices or channels of the second textured region at a second rate, thereby allowing the cream to flow through the textured regions at the same or different rates.

The kit 50 and/or thimble module 530J can include instructions for using the thimbles.

The dexterity pad module 530K includes different shaped objects and corresponding locations/slots for placing each object. The locations and/or slots are configured to require increasing need for motion, sensibility, strength and/or dexterity, thus training and exercising the patient. In operation, the patient places each object in a corresponding recessed area or slot, which requires fine motor skill, to improve dexterity and function. The development of these skills and strength is generally gradual and utilizes both intrinsic and extrinsic muscles. The kit 50 and/or dexterity pad module 530K can include instructions for using the dexterity pad. In some embodiments, one or more objects in the dexterity module 530K include pressure sensors to detect force, pressure, and/or surface area. Data from the pressure sensors can be used to monitor compliance (or noncompliance) with a treatment plan, as discussed below.

Figure 7:
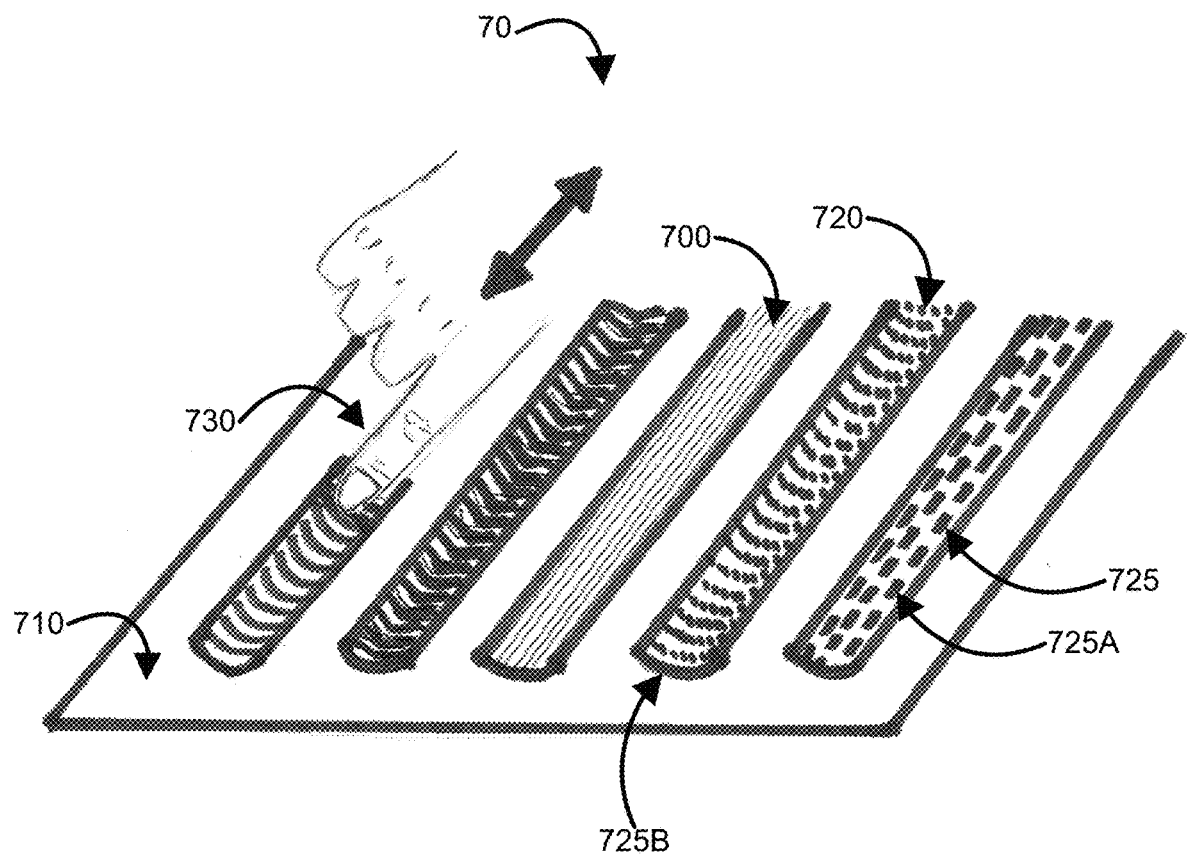
FIG. 7 illustrates a perspective view of a scar revision system.

FIG. 7 illustrates a perspective view of a scar revision module 70 that can be integrated onto the housing of the kit. The scar revision module 70 includes a plurality of elongated channels 700 defined in a surface 710. The channels 700 include one or more textured regions 720 of varying coarseness. The coarseness is defined by features 725 having a respective shape. For example, a feature 725A with a larger shape is coarser than a feature 725B with a smaller shape. The features 725 can be raised or lowered with respect to the surface of each channel 700. In addition, the features 725 can be oriented in the same or different directions, which can define a pattern. The features 725 can also be regularly or irregularly spaced along and/or across the channels 700. In operation, the user can slide a scar tissue on a finger 730 (or other body part) along one or more textured regions 720 to treat the scar (e.g., to reduce sensitivity thereof), similar to the thimble module described above. In some embodiments, the scar revision module 70 is integrated onto a working surface or a lid of the kit. In some embodiments, one or more pressure sensors are embedded in the surface 710 of the scar revision module 70 to detect force, pressure, and/or surface area. Data from the pressure sensors can be used to monitor compliance (or noncompliance) with a treatment plan, as discussed below.

Therefore, a system, which may be provided in the form of a portable kit, is described for therapy to a patient's fingers and/or hand. The system includes a housing, case or enclosure adapted for and having inclusions and extensions supporting the above-described elements and others. In an aspect, the system is integrated into a briefcase-shaped housing. The housing includes an outer shell body (e.g., plastic, wood, metal). The housing has an inner surface and at least one platform or working surface or platform built therein which supports the plurality of therapy modules described. The inner structure of the housing or case includes one or more flat platforms with recessed modules for various types of therapeutic activity. Also, the system folds onto itself and can be portable (e.g., for carrying while travelling).

With proper instructions, a patient can take the kit home (or while travelling) and use it to perform therapy exercises without having to come in to a clinic or facility to actively perform the exercises there. This saves time and money for the patient because he or she does not have to travel, park, check in at a clinic and wait for a practitioner to assist them, or pay co-pays or co-insurance. It is believed that the kit can decrease healthcare costs at a population level.

Assistance with the kit can be in the form of written or verbal instructions or other preparation provided to the patient remotely so the system can be used at home. This is especially important for patients without the means to travel or for the elderly or disabled.

Figure 8:
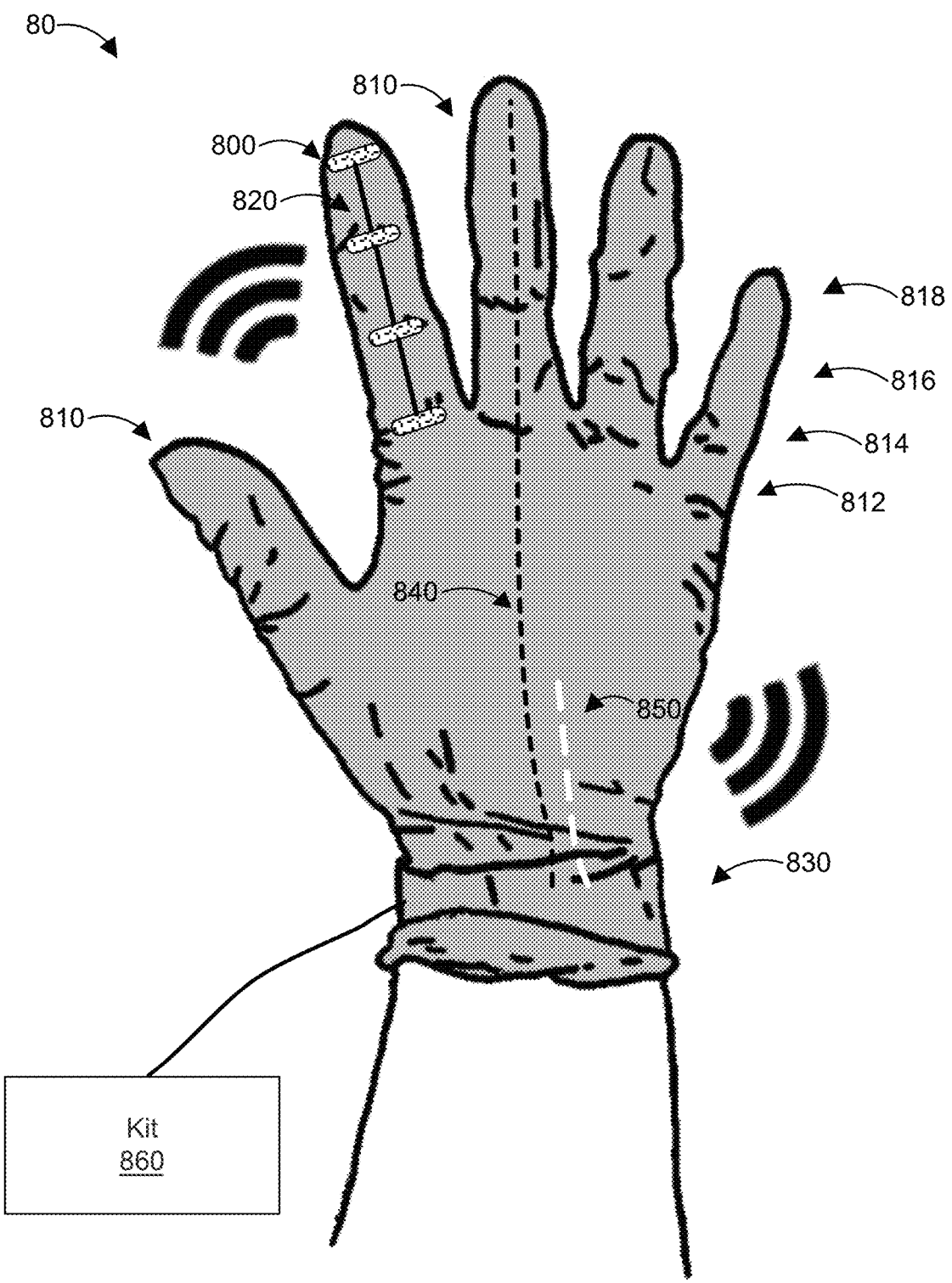
FIG. 8 is a top view of a therapeutic tracking glove according to one or more embodiments.

FIG. 8 is a top view of a therapeutic tracking glove 80 according to one or more embodiments. The glove 80 can be included in a hand therapy kit, such as kit 10, 20, 50, and/or 2000. The glove 80 can be placed on a user's hand during physical therapy to collect data regarding the range of motion of the user's hand. The glove 80 includes a plurality of rotational position sensors 800 that are attached to the glove fingers 810 at positions 812, 814, 816, 818 that correspond to the three joints or rotation points of the user's fingers and the user's fingertip. For example, position 812 corresponds to the base of the glove finger 810, which corresponds to the metacarpophalangeal joint; position 814 corresponds to the middle joint of the user's finger (i.e., the proximal interphalangeal joint); position 816 corresponds to the joint closest to the user's fingertip (i.e., the distal interphalangeal joint); and position 818 corresponds to the user's fingertip. Each sensor 800 is mechanically coupled to a wire or rod 820 that extends between adjacent sensors 800. Each sensor 800 can rotate about an axis (e.g., similar to a hinge) such that the angle between adjacent rods 820 can vary according to the rotational position of the sensor 800.

When the user's fingers and glove fingers 810 bend inwardly, the rods 820 move with respect to the sensors 800. The movement of the rods 820 causes the sensors 800 to rotate so that the rods 820 continue to extend between adjacent sensors. As the user engages in physical therapy exercises while wearing glove 80, the sensors 800 detect their rotational positions which correspond to the angle of rotation of the respective joints in the user's fingers. It is noted that sensors 800 are examples and other sensors can be used as would be appreciated by those skilled in the art. For example, the type and/or position of the sensors 800 can be modified as technology improves.

FIG. 8 also illustrates an elastic band 840 that is attached to a glove 80 fingertip and extends from the glove 80 fingertip to a wrist band 830. As the user engages in physical therapy exercises, the length of the elastic band 840 slides towards or away from wrist band 830 according to the finger's position. For example, when the hand is closed (e.g., like a fist), the elastic band 840 is pulled away from the wrist band 830 due to the motion of the finger. When the hand is opened (e.g., as illustrated in FIG. 8), the elastic band 840 is pulled towards the wrist band 830 due to the elasticity of the elastic band 840 since a shorter length of elastic band 840 is needed. As the elastic band 840 moves back and forth, its position or length is sensed by a sensor disposed in wrist band 830. Thus, the output of the sensor corresponds to the finger's ability to extend and retract.

Each glove 80 finger 810 can include a corresponding elastic band 840, and the position or length of each such elastic band 840 can be measured by a respective sensor in wrist band 830. Only one elastic band 840 is illustrated in FIG. 8 for clarity.

A second elastic band 850 is attached to the glove 80 palm and extends from the glove 80 palm to wrist band 830. Elastic band 850 functions in the same way as elastic band 840, but elastic band 850 is used to measure the range of motion of the user's wrist during wrist extension and retraction exercises. A corresponding sensor to measure the position or length of elastic band 840 is disposed in wrist band 830.

The wrist band 830 houses electrical components, such as a microprocessor, a communication interface, and a battery. The microprocessor receives data from the sensors 800 (e.g., via a wired connection) and transmits the data to an external device over the communication interface. The communication interface can include a wired communication interface and/or a wireless communication interface. The wireless communication interface can include a wireless radio, such as a WiFi radio, a cellular radio, and/or a Bluetooth radio. The wired communication interface can include a USB port, a serial port, and/or an Ethernet port to connect the wrist band 830 to an external device, as kit 860. Kit 860 can be the same as kit 10, kit 20, and/or kit 50. Kit 860 can include a wireless and/or a wired communication interface to further transmit the data, for example to the user's physical therapist and/or to the user's mobile device (e.g., to be accessed by an app on the user's mobile device, as discussed below).

It is noted that although FIG. 8 illustrates that the rotational position sensors 800, rods 820, and elastic bands 840, 850 are disposed on the back side of glove 80, corresponding to the back of the user's hand, it is noted that any or all of these components can be disposed on the front side of glove 80, corresponding to the front of the user's hand.

Figure 9:
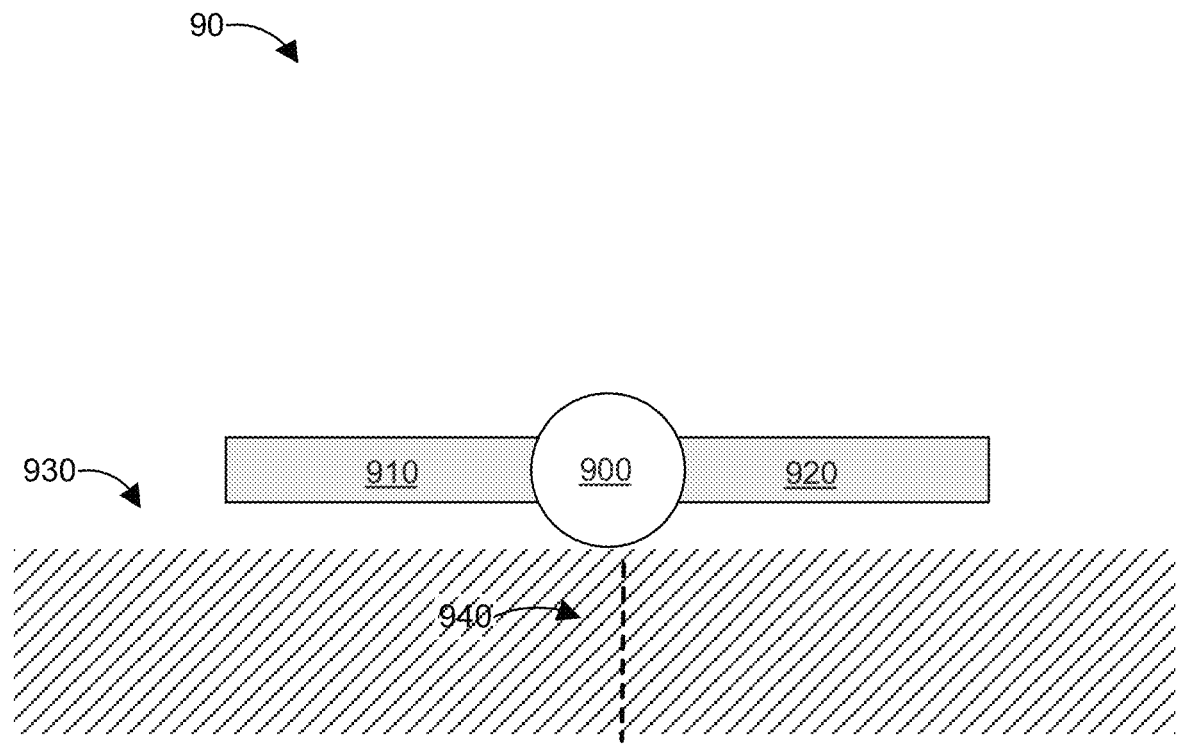
FIG. 9 illustrates a sensor apparatus for measuring the angle of rotation of a finger joint according to one or more embodiments.
Figure 10:
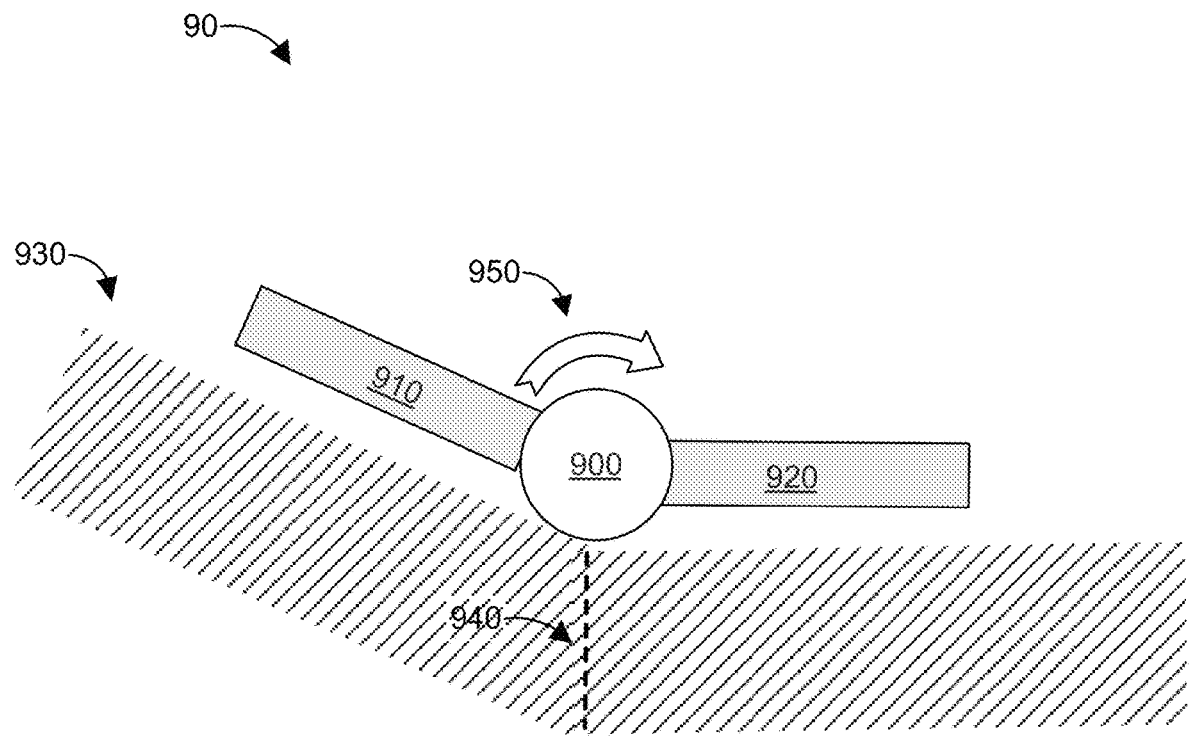
FIG. 10 illustrates the sensor apparatus of FIG. 9 when the glove finger is in a bent state.

FIG. 9 illustrates a sensor apparatus 90 for measuring the angle of rotation of a finger joint according to one or more embodiments. The apparatus 90 includes a rotational position sensor 900 that is mechanically coupled to first and second rods 910, 920. The apparatus 90 is placed on a finger of a glove 930 worn by the user with the rotational position sensor 900 attached or fixed to a position 940 on the finger portion of the glove 930 that corresponds to a finger joint. When the user flexes a joint in her finger inwardly, the position of the rods 910, 920 changes with respect to sensor 900, as illustrated in FIG. 10. The change in position of the rods 910, 920 causes the rotational position sensor 900 to rotate 950 about an axis that extends through its center and that passes into and out of the page of FIG. 10. The output of the rotational position sensor 900 corresponds to the angle of rotation of the finger joint.

Sensor 900 can be the same as or different than sensor 800. In addition, rods 910, 920 can be the same as or different than rods 820. Further, glove 930 can be the same as or different than glove 80.

Figure 11:
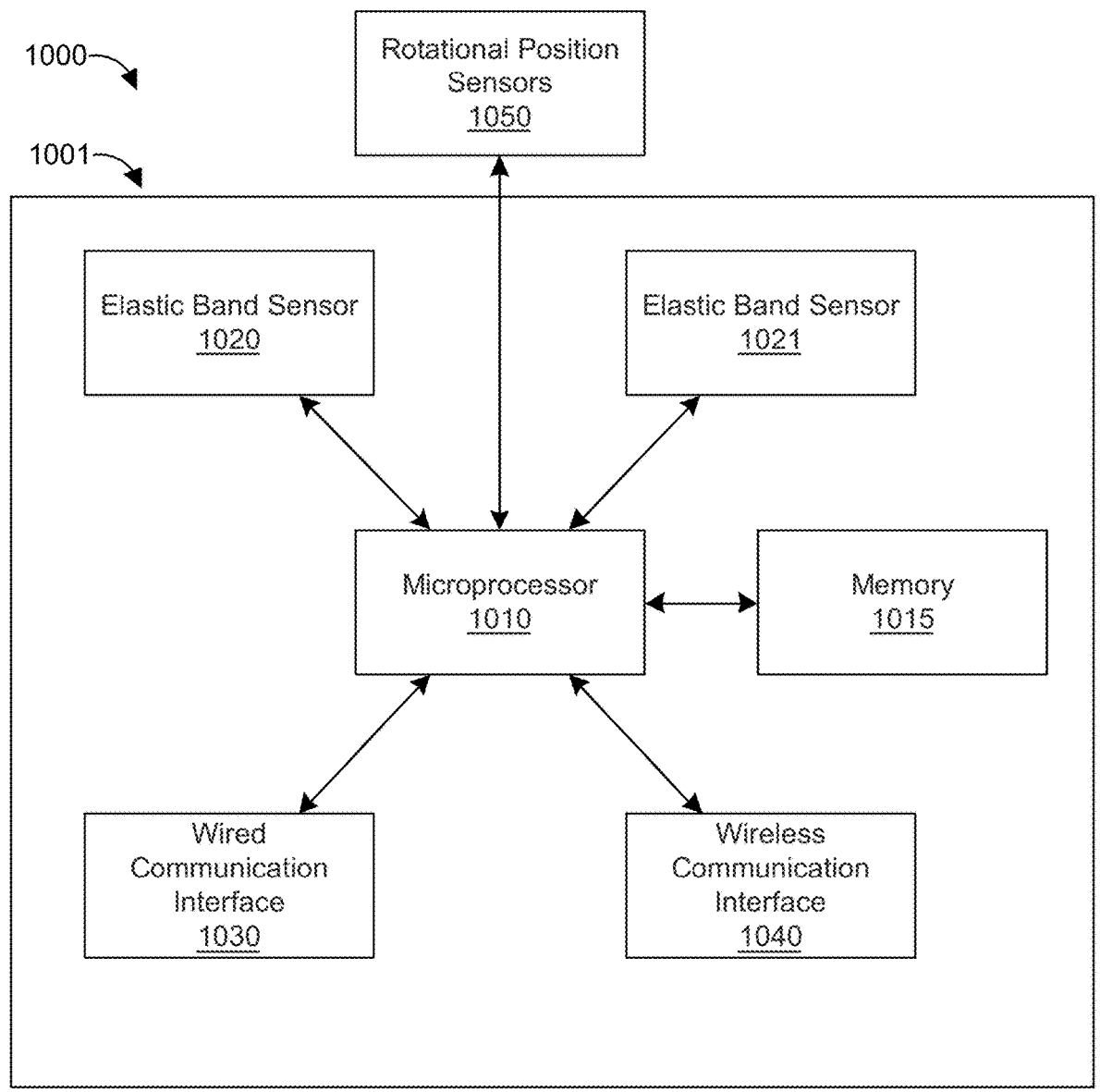
FIG. 11 is a block diagram of the electrical components of a wrist band 1000 according to one or more embodiments.

FIG. 11 is a block diagram of the electrical components of a wrist band 1000 according to one or more embodiments. The wrist band 1000 can be the same as or different than wrist band 830. Wrist band 1000 includes a microprocessor 1010, elastic band sensors 1020, 1021, a wired communication interface 1030, and a wireless communication interface 1040, which are disposed in a housing 1001. The microprocessor 1010 is in electrical communication with the elastic band sensors 1020, 1021 and with each of the rotational position sensors 1050, for example over a wired connection. Rotational position sensors 1050 can be the same as or different than rotational position sensors 800 and/or 900, discussed above. The microprocessor 1010 receives output signal data from the elastic band sensors 1020, 1021 and the rotational position sensors 1050 and transmits the data to an external device (e.g., a server, a laptop, a mobile device (e.g., a smartphone), a tablet, etc.) over a wired communication interface 1030 or a wireless communication interface 1040. The wireless communication interface 1040 includes a radio and a modem to transmit the data wirelessly (e.g., over a WiFi communication network, over a cellular communication network, and/or over a Bluetooth connection). The wired communication interface can include a serial port, an Ethernet port, or other port. The microprocessor 1010 can temporarily store the output signal data in memory 1015 prior to transmitting the data over one of the communication interfaces 1030, 1040.

Figure 12:
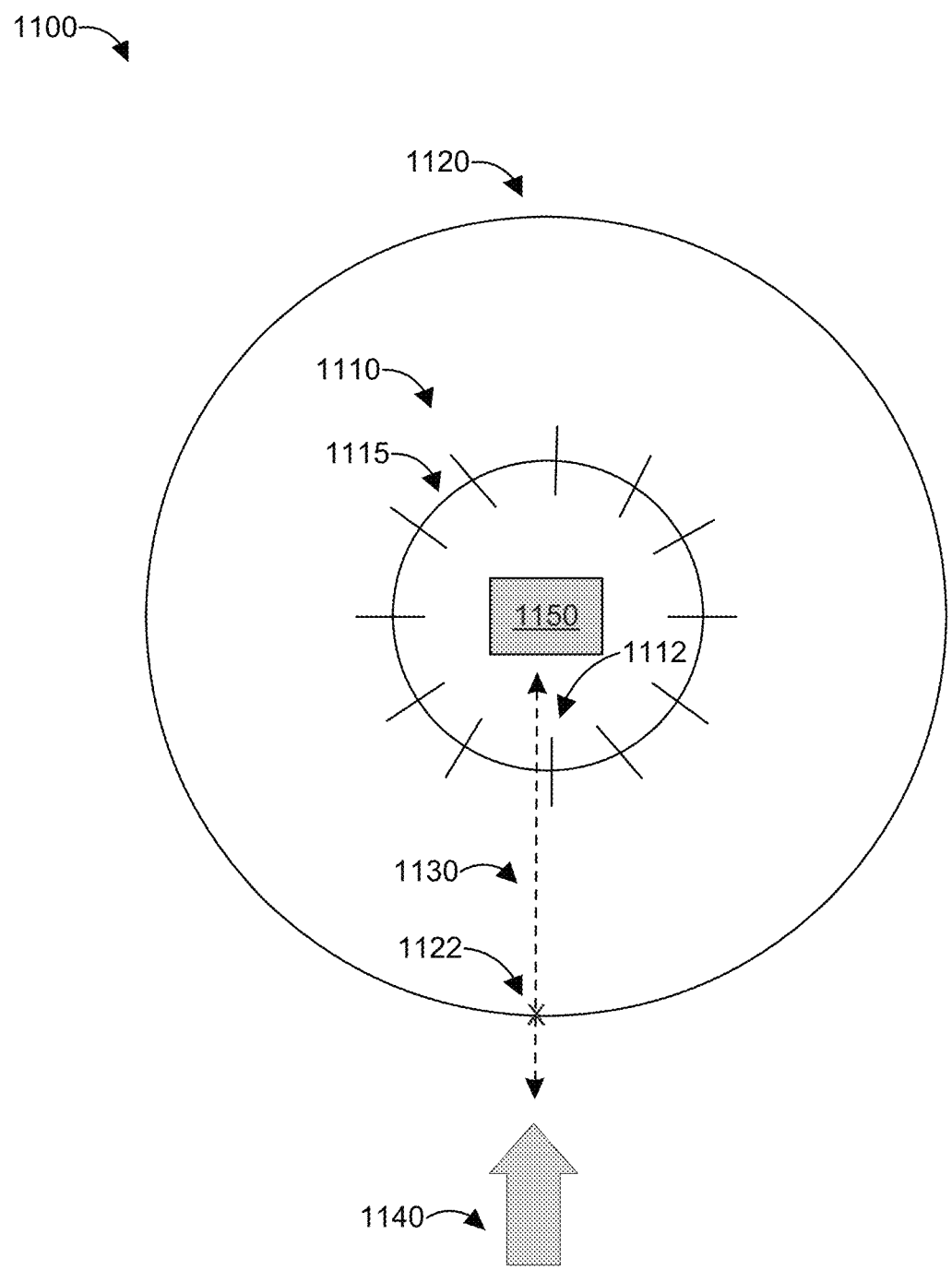
FIG. 12 illustrates a pressure sensor ball according to one or more embodiments.

FIG. 12 illustrates a pressure sensor ball 1100 according to one or more embodiments. The sensor ball 1120 can be included in a hand therapy kit, such as kit 10, 20, 50, and/or 2000. The sensor ball 1120 is sized to fit in a user's hand to measure the user's grip strength. The pressure sensor ball 1100 includes an array of radial force sensors 1110 disposed in a compressible ball 1120. The compressible ball 1120 can be formed out of a compressible material, such as rubber, synthetic rubber, a gel, or other material.

Grip strength can be calculated as well as pinch strength using a pressure transducer within a compressible medium, such as foam, putty, or other similar material. The sensor would function as a dynamometer. This detects changes in force measured in pounds or kilograms. The data received from these sensors would be transmitted to a recording device, either through wireless or wired means. This data is stored and organized using an algorithm that categorizes the information. The algorithm may be encoded in a set of machine stored and machine read program instructions in a memory unit and executed on a processing circuit. This information may then be referred back to or communicated to the physician or therapist, in order to monitor progress and help patients achieve targets or goals.

The radial force sensors 1110 may be disposed about an inner spherical body 1115. This body can likewise by a variation on a spherical shape, e.g., having an oval or elliptical or similar profile. At least a portion of each radial force sensor 1110 can slide inwardly in response to a force along the radius or axis on which the radial force sensor 1110 is aligned. For example, radial force sensor 1112 is disposed parallel to and is generally aligned with axis 1130 which extends radially through inner ball 1115 and compressible ball 1120. Radial force sensor 1112 and axis 1130 can be co-axial, but they are not illustrated as such in FIG. 12 for clarity.

The inward distance that each radial force sensor 1110 slides (e.g., its displacement) is proportional to the force applied along the axis or radius of alignment. For example, radial force sensor 1112 slides inwardly and parallel to axis 1130 when an inward force 1140 is applied at point 1122 on the compressible ball 1120. When the inward force 1140 is released, radial force sensor 1112 returns to its initial state. Thus, the radial force sensors 1110 can sense the direction and magnitude of the force applied to the compressible ball 1100, such as when a user squeezes the compressible ball 1100 to measure a hand's grip strength. The data output of the radial force sensors 1110 can correspond to a map of where a hand's grip strength is relatively high and where a hand's grip strength is relatively low (or zero).

The radial force sensors 1110 are distributed across the outer surface of the inner spherical body 1115 such that the radial force sensors 1110 can sense an inward force from any location on the outer surface of the compressible ball 1120. The number (and density) of radial force sensors 1110 can be increased to provide a higher resolution of a hand's grip strength, and it can be lowered to provide a lower resolution of a hand's grip strength. In some embodiments, the radial force sensors 1110 are push-pin sensors.

The radial force sensors 1110 are in electrical communication with electrical components 1150, including a microprocessor, a communication interface, and a battery. The microprocessor receives data from the radial force sensors 1110 (e.g., via a wired connection) and transmits the data to an external device over a wireless communication interface. The wireless communication interface can include a wireless radio, such as a WiFi radio, a cellular radio, and/or a Bluetooth radio.

Figure 13:
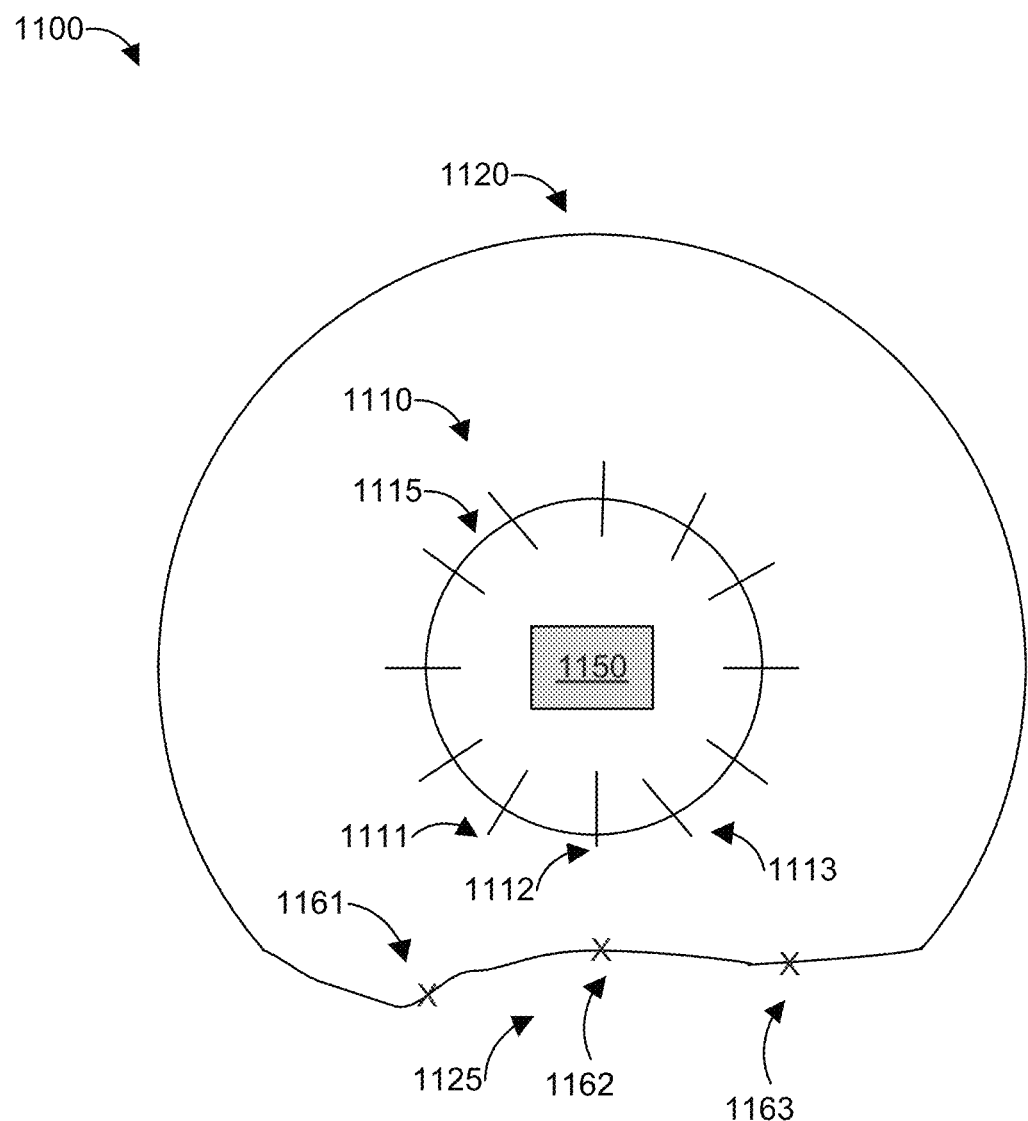
FIG. 13 illustrates the pressure sensor ball of FIG. 12 in a compressed state according to one or more embodiments.

FIG. 13 illustrates pressure sensor ball 1100 in a compressed state according to one or more embodiments. In the compressed state in the FIG. 13 example, a force is applied to the bottom of pressure sensor ball 1100 which causes a deformation in region 1125 of compressible ball 1120. As a result of the force applied to the pressure sensor ball 1110, radial force sensors 1111-1113 are displaced inwardly along their respective axes of orientation. Radial force sensor 1112 is displaced inwardly more than radial force sensors 1111, 1113 because a greater force is applied the compressible ball 1120 at point 1162 than at points 1161, 1163. If the forces were created when a user's fingers were placed on the pressure sensor ball 1100 at points 1161-1163, the output of the radial force sensors 1111-1113 would indicate that the finger placed at point 1162 created a larger force than the fingers placed at points 1161, 1163. This can be useful feedback for the user (and his/her physical therapist) to determine which fingers are weak and may need additional physical therapy.

In some embodiments, the external computer that receives the data from the pressure sensor ball 1100 can determine the pressure applied by the user's hand. Since pressure is a function of force and area, the external computer would need to determine the area over which the force was applied to determine the pressure. The surface area over which the force was applied, on compressible ball 1120, is proportional to the number of radial force sensors 1110 that sensed a force and the density of the radial force sensors 1110 on the inner spherical body 1115.

Figure 14:
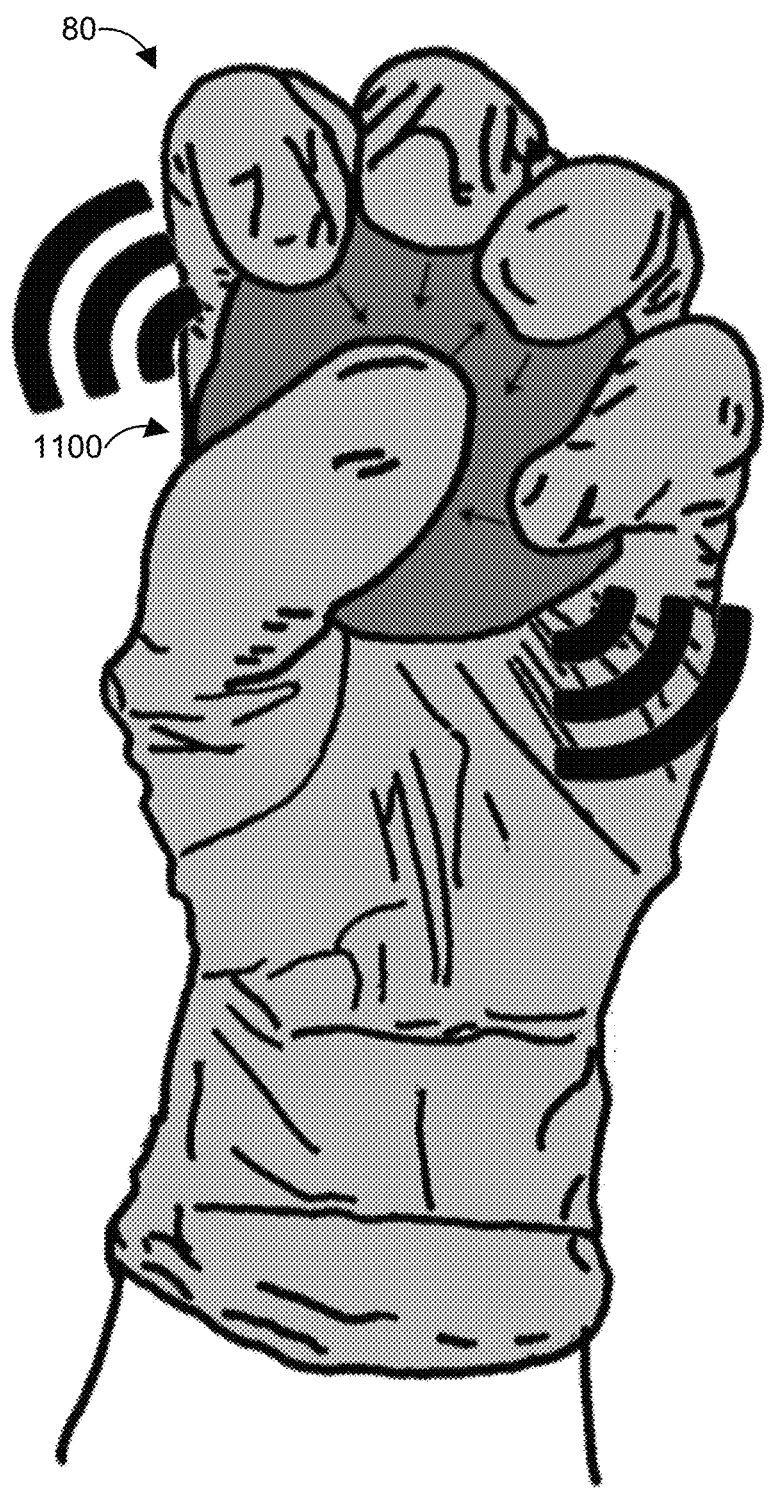
FIG. 14 illustrates an embodiment where the therapeutic tracking glove and the pressure sensor ball are used in therapy together to provide additional data regarding physical therapy exercises.

FIG. 14 illustrates an embodiment where the therapeutic tracking glove 80 and the pressure sensor ball 1100 are used in therapy together to provide additional data regarding physical therapy exercises.

Figure 15:
FIG. 15 illustrates an example screenshot from an app running on a user's mobile device according to one or more embodiments.

FIG. 15 illustrates an example screenshot 1500 from an app (i.e., an application program) running on a user's mobile device 1501 according to one or more embodiments. In screenshot 1500, the app displays data collected from a therapeutic apparatus and reformatted for presentation to the user. The therapeutic apparatus can include the tracking glove 80 and/or the pressure sensor ball 1100 discussed above. For example, screenshot 1500 can illustrate historical data 1510 of the average angle of extension or retraction of a user's wrist over a given time period (e.g., days, weeks, etc.). This feature allows the user to track his/her progress and to recognize when the physical therapy exercises are helping (or not helping).

Screenshot 1500 illustrates additional feature of the app. For example, screenshot 1500 illustrates a send data button 1520 that allows the user to send some or all of the data collected from the therapeutic apparatus(es) to another party, such as a doctor or a physical therapist. Screenshot also illustrates a sync button 1530 for connecting the user's mobile device 1501 to a given therapeutic apparatus for data collection. The user can switch from syncing the mobile device 1501 with a first therapeutic device to a second therapeutic device using sync button 1530.

Figure 16:
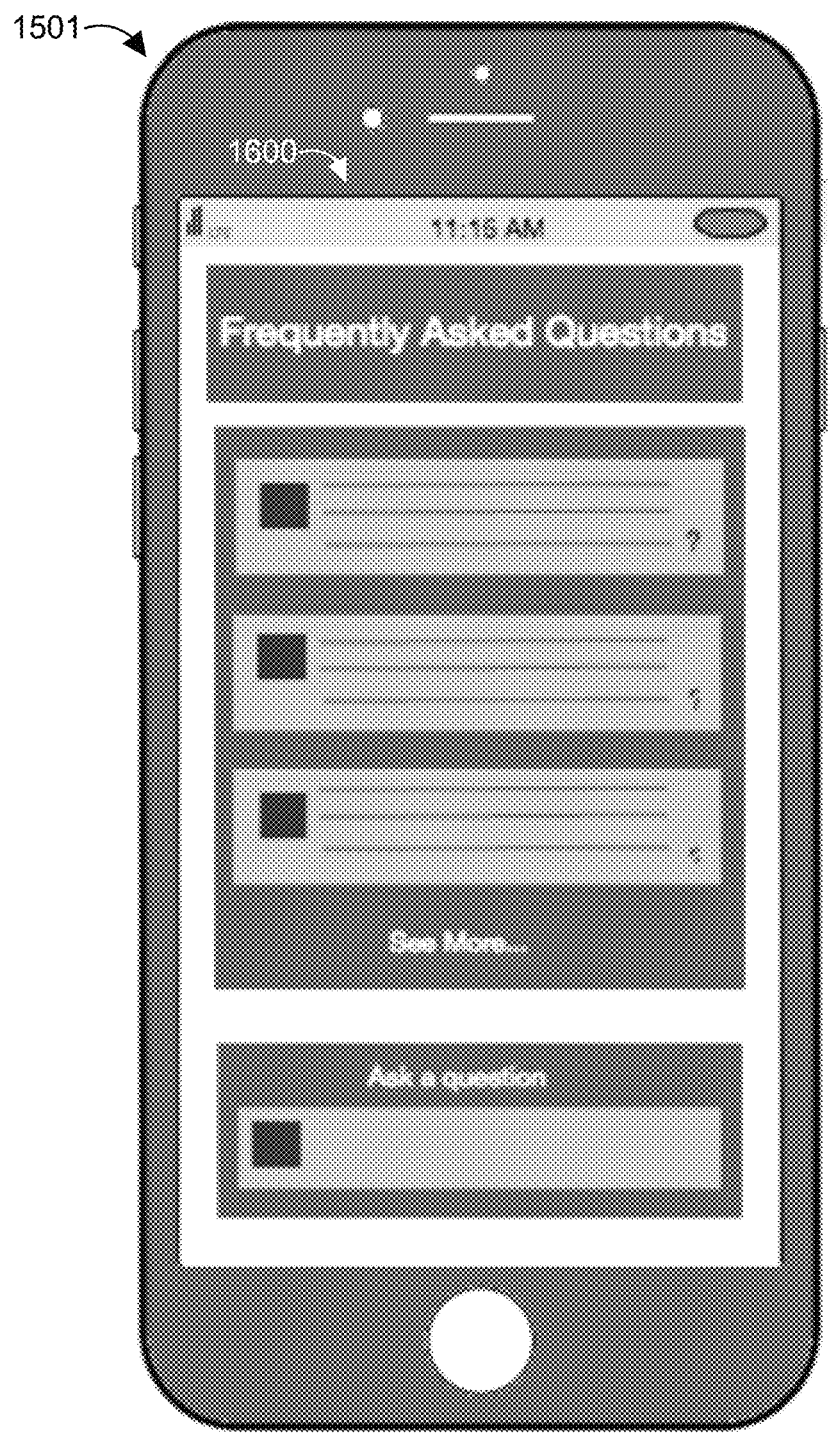
FIG. 16 illustrates an optional screenshot from the app according to one or more embodiments.

FIG. 16 illustrates an optional screenshot 1600 from the app according to one or more embodiments. In screenshot 1600, the user can view frequently asked questions, can ask a question (e.g., to his/her physical therapist and/or to others undergoing physical therapy), and can engage in social and/or motivational activities. For example, the app can include a video and/or an audio component for the user to receive instructions on how to perform a physical therapy exercise. The app an also includes a "points" counter where the user acquires points for each set or repetition of a physical therapy exercise.

Figure 17:
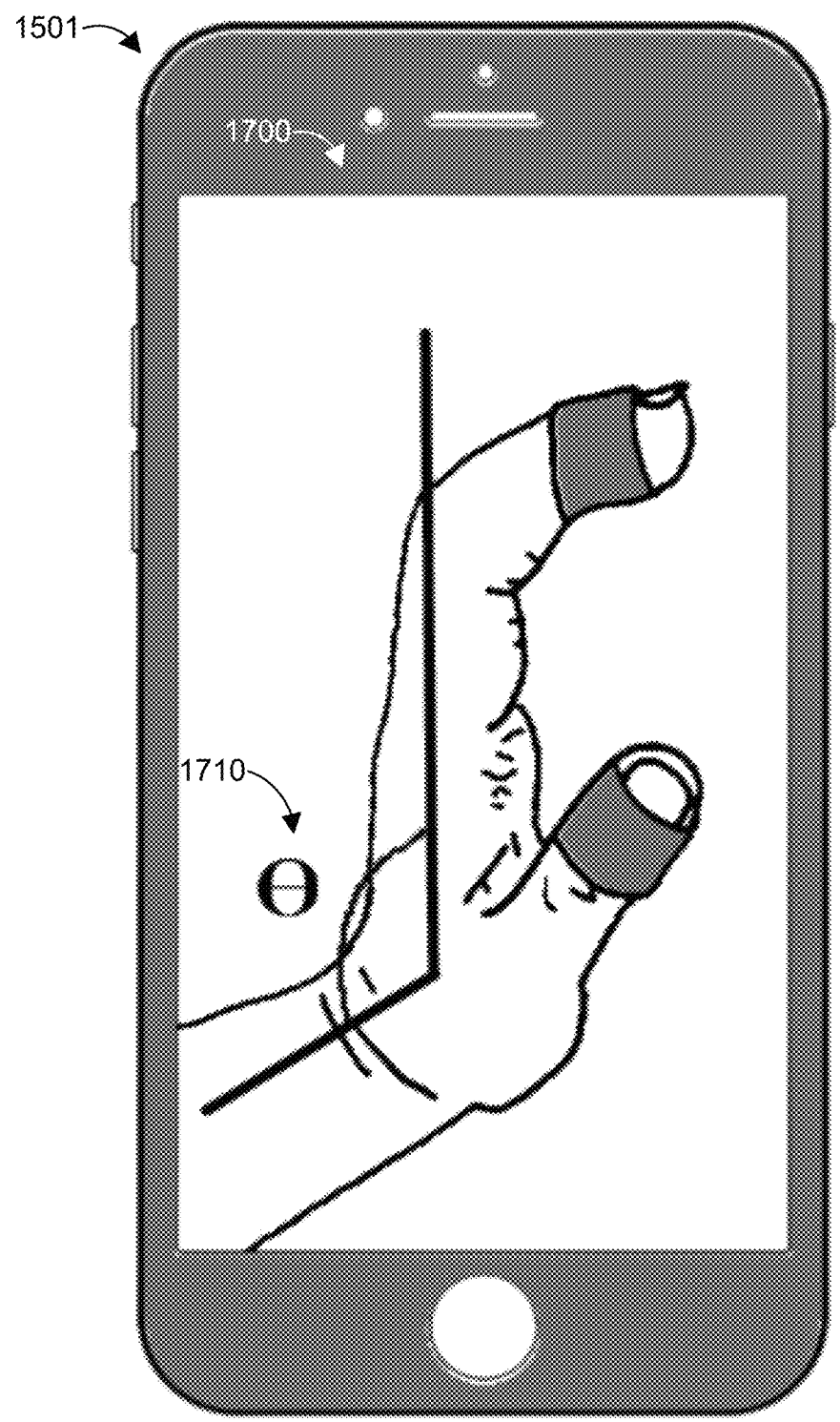
FIG. 17 illustrates another screenshot from the app according to one or more embodiments.

FIG. 17 illustrates another screenshot 1700 from the app according to one or more embodiments. In screenshot 1700, a user performs a physical therapy exercise with a hand (e.g., retracting his/her wrist) while capturing an image or video of the hand and wrist using the camera on the mobile device 1501. The app can determine the angle of retraction 1710 by detecting the position of the user's forearm and fingers. The app can be programmed by processing a plurality of images of user's hands and wrists in different orientations using machine learning or cluster recognition.

Figure 18:
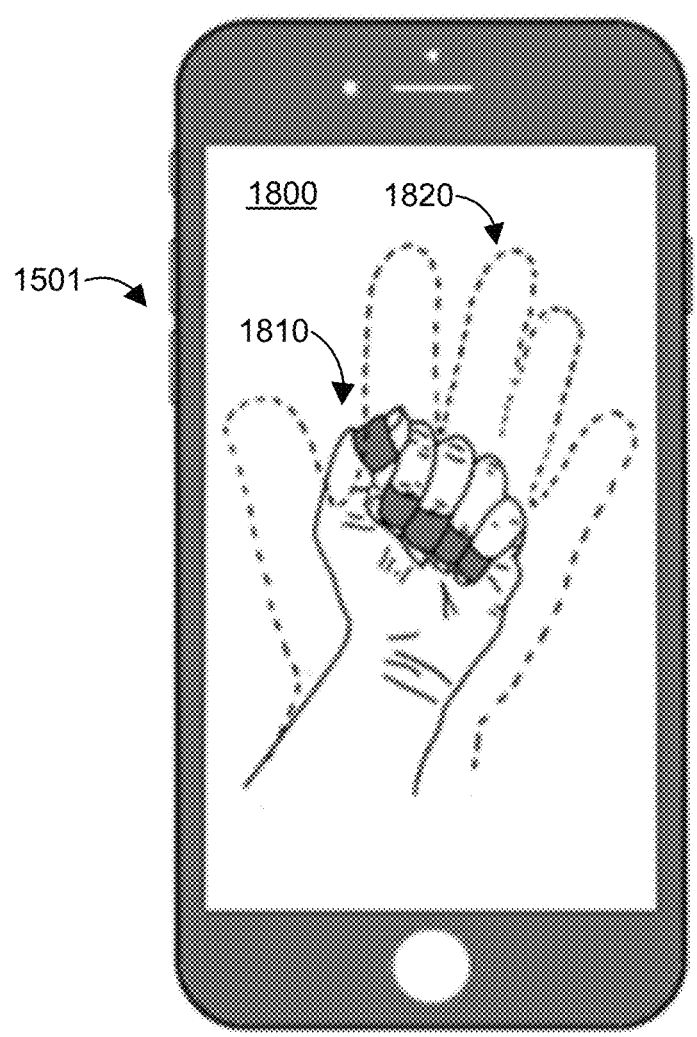
FIG. 18 illustrates another screenshot from the app according to one or more embodiments.
Figure 19:
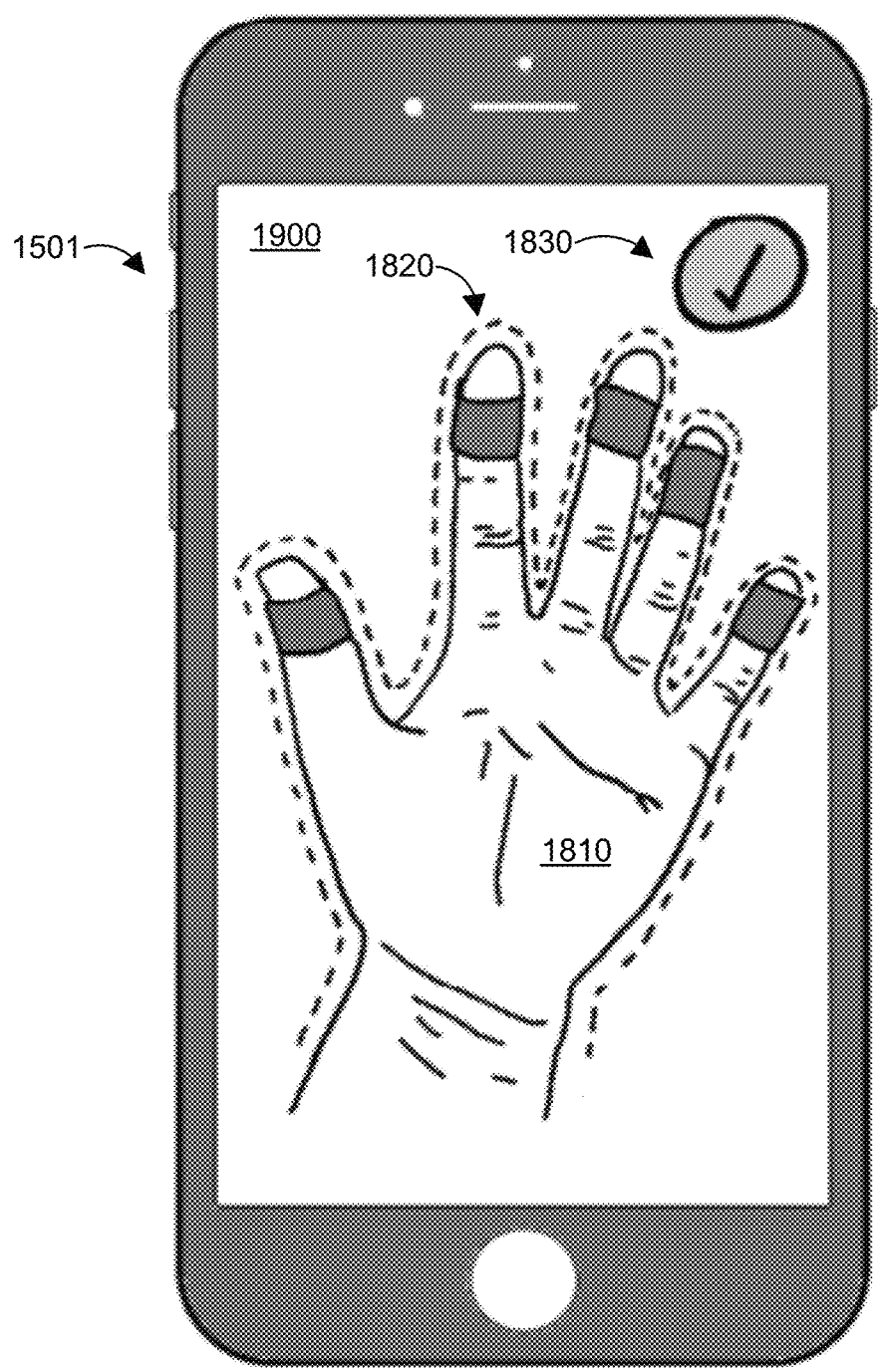
FIG. 19 illustrates another screenshot from the app according to one or more embodiments.

FIG. 18 illustrates another screenshot 1800 from the app according to one or more embodiments. In screenshot 1800, a user performs a physical therapy exercise with a hand 1810 (e.g., opening his/her hand) while capturing an image or video of the hand 1810 using the camera on the mobile device 1501. The app can overlay an outline 1820 of a hand in the open position with the image of the user's hand 1810 as a guide and as motivation for the user while performing the exercise. The app can recognize the position of the user's hand 1810 can visually indicate 1830 when the user's hand 1810 matches the outline 1820 and is in the correct position (e.g., fully opened), as illustrated in screenshot 1900 in FIG. 19. In addition or in the alternative, the app can audibly indicate when the user's hand matches the outline 1820 and is in the correct position.

Figure 20:
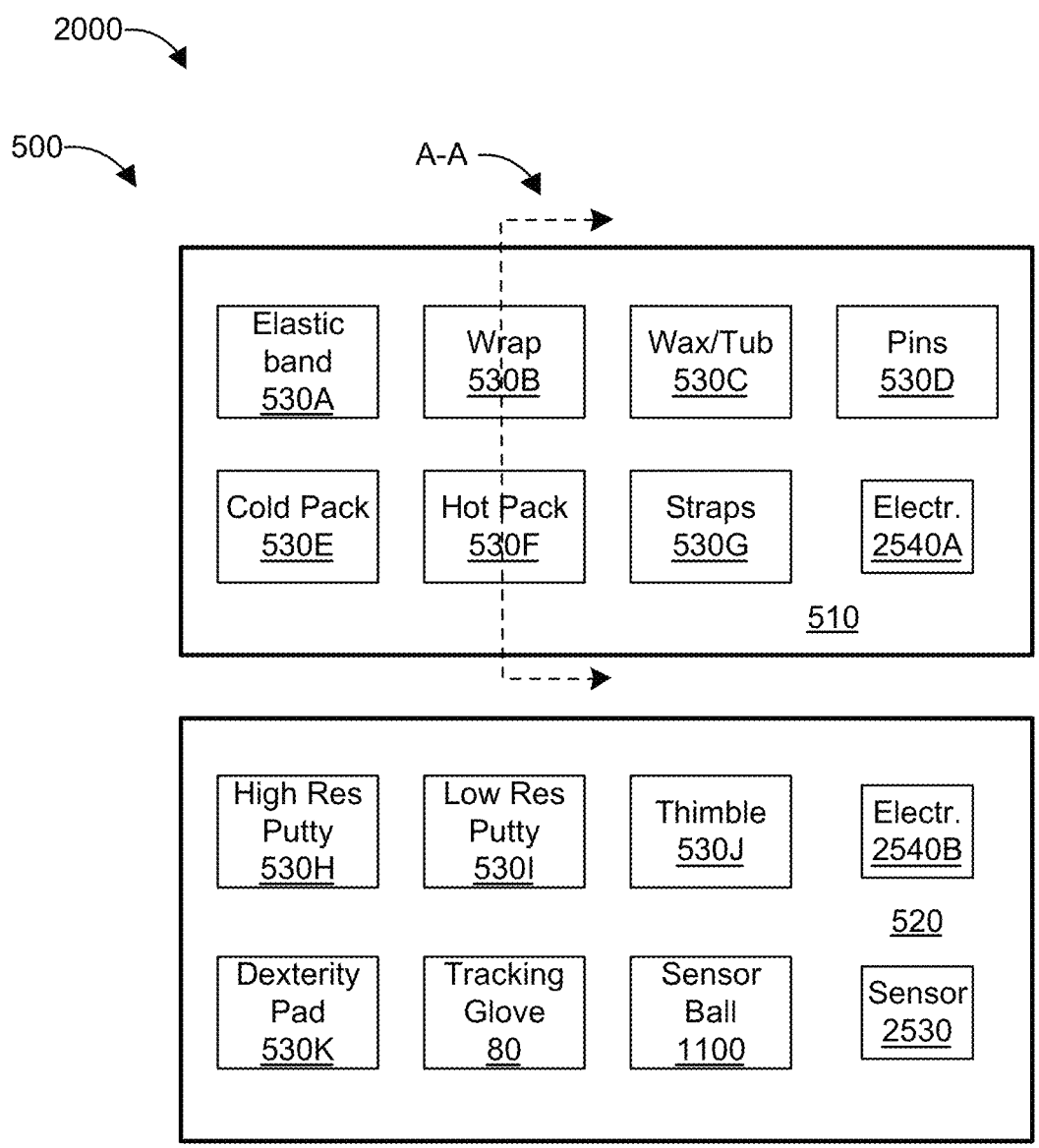
FIG. 20 illustrates a plan view of a kit according to one or more embodiments.

FIG. 20 illustrates a plan view of a kit 2000 according to one or more embodiments. The kit 2000 includes a plurality of modules and components that are integrated into a housing, case or enclosure which is portable, cost-efficient and suited for the present purpose.

The kit 2000 includes a housing 500 having an upper lid 510 and a lower lid 520 as generally described above. Kit 2000 is the same as kit 50 but with the addition of therapeutic tracking glove 80 and pressure sensor ball 1100. In some embodiments, kit 2000 includes therapeutic tracking glove 80 but does not include pressure sensor ball 1100. In other embodiments, kit 2000 includes pressure sensor ball 1100 but does not include therapeutic tracking glove 80. The modules 530 can be removable and/or interchangeable as in kit 50.

The kit 2000 can optionally include a housing sensor 2530 that can detect whether the housing 500 is opened (or unfolded) or closed (folded) (e.g., in an opened or closed state). For example, the housing sensor 2530 can include a light sensor that detects light when the housing 500 is opened and does not detect light when the housing 500 is closed. In addition or in the alternative, the housing sensor 2530 can include first and second electrodes 2540A, 2540B on the upper lid 510 and lower lid 520, respectively. The first and second electrodes 2540A, 2540B can be in electrical contact when the housing 500 is closed and they can be spaced apart (and not in electrical contact) when the housing 500 is opened. Thus, the detection of current and/or voltage in a circuit (e.g., with a current sensor and/or a voltage sensor) that includes the first and second electrodes 2540A, 2540B can be used to determine whether the housing 500 is opened or closed.

Figure 21:
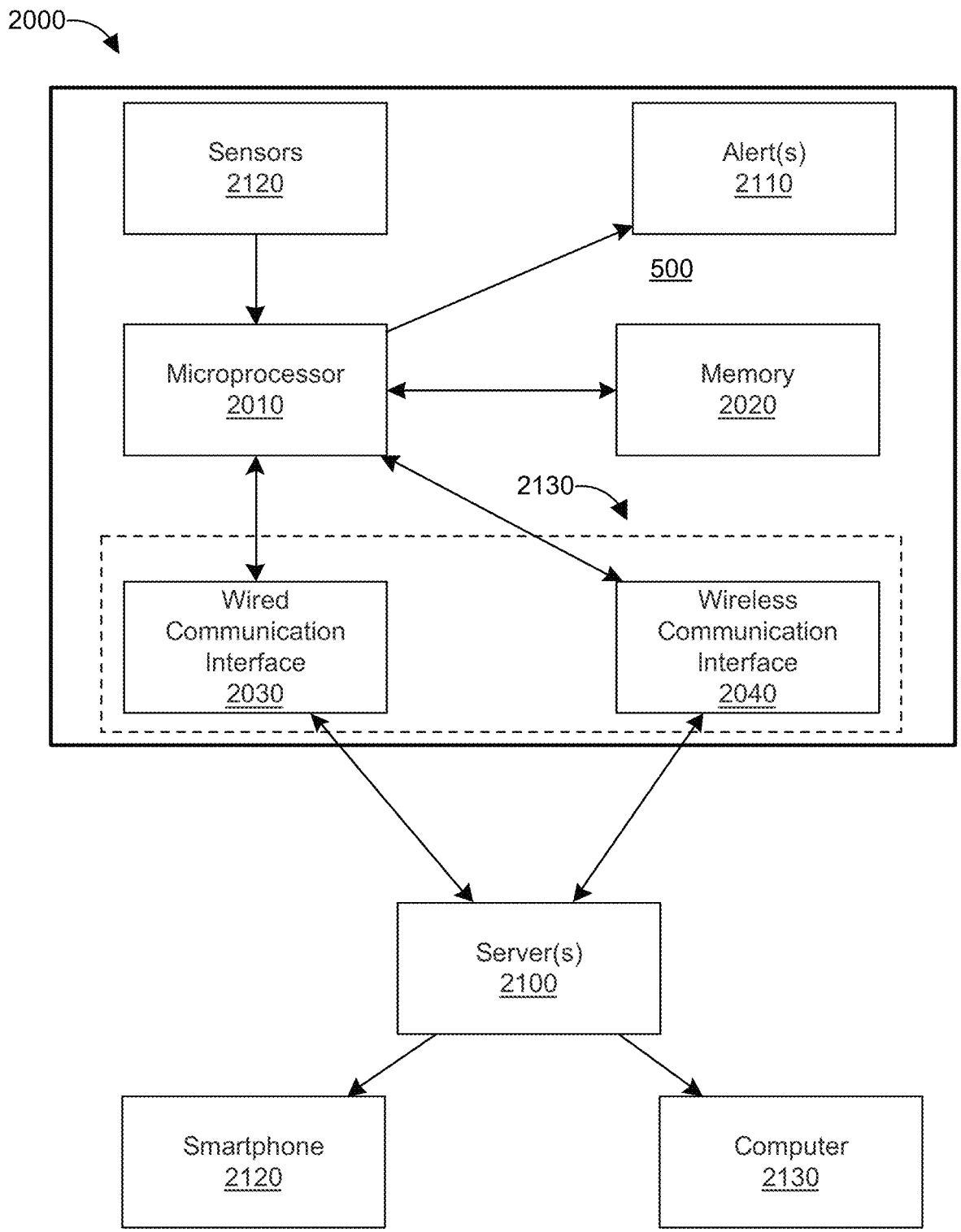
FIG. 21 is a block diagram of optional electronic components in the kit of FIG. 20 and optional external devices.

Kit 2000 includes optional electronic components as illustrated in FIG. 21 and optional external devices. For example, kit 2000 can include a microprocessor 2010, a memory 2020, a wired communication interface 2030, and/or a wireless communication interface 2040. The kit 2000 can receive data from one of the modules 530 over one of the communications interfaces 2030, 2040 to further transmit (over one of the communications interfaces 2030, 2040) to one or more remote computers or servers 2100 (e.g., to be accessed by the user, her physical therapist, or another party, such as an insurance agency or a third-party verification service) or another device, such as the user's personal computer 2130 (e.g., a laptop, a desktop, a mobile phone (e.g., a smartphone 2120), a tablet, etc.) where it can be accessed, analyzed, and/or displayed by an application running on the user's personal computer 2130 (e.g., as described above).

In a specific example, kit 2000 receives data from one of the modules 530 (e.g., glove 80 or ball 1100) over wired communication interface 2030 and then transmits the data over the wireless communication interface 2040 to the user's personal computer and/or to the server(s) 2100. This can allow the modules (e.g., glove 80 and/or ball 1100) to be constructed without wireless communication interfaces, which allows them to be simpler and less expensive. The processor 2010 receives and transmits the data as discussed above. The processor 2010 can temporarily store some or all of the data in memory 2020, for example as data is received or prior to retransmission.

In another example, the microprocessor 2010 receives sensor data from sensors 2120, which can include any of the sensors discussed herein (e.g., including the module presence sensors 2230, the container presence sensors 2720, and/or the lid sensors 2750). In an example, a dexterity pad module (e.g., 530K below) is coupled, mechanically and/or electrically, with such presence sensors 2230 and/or pressure sensors or other sensors to determine the use of or the nature of use of the dexterity pad module. This is true for other components of the present kit as well, as suits a given implementation. The microprocessor 2010 temporarily store the sensor data in memory 2020 and then transmit the sensor data to server(s) 2100 via communications interface 2130, which includes wired communication interface and/or wireless communication interface 2040. In some embodiments, sensors 2120 includes a biometric sensor disposed on the housing. The biometric sensor can be used to confirm the patient's identity, which can be performed periodically and/or in the event of noncompliance with a treatment plan.

One or more alerts 2110 can be disposed in the kit 2000. The alert(s) 2110 can include a light source (e.g., an LED) and/or an audio source (e.g., a speaker). The alert(s) 2110 can be activated through commands received from the microprocessor 2010, which can further receive commands from the server(s) 2100. The microprocessor 2010 and/or the server(s) 2100 can analyze data (or lack thereof) received from modules 530 to determine whether to generate an alert 2110. For example, the microprocessor 2010 and/or the server(s) 2100 can receive a treatment plan (e.g., generated by a physical therapist) that indicates which modules 530 the patient needs to use to perform the prescribed physical therapy exercises, the frequency of such physical therapy exercises, and/or the number of repetitions of such physical therapy exercises. If the data from the modules 530 (or lack thereof) indicates that the patient is not performing the physical therapy exercises as directed, the microprocessor 2010 and/or the server(s) 2100 can generate an alert 2110, which can be based on the variance with the treatment plan. For example, if it appears that the patient forgot to perform an exercise, the alert 2110 (e.g., a first alert) can include a first light having a first color, intensity, and or blinking frequency. In addition or in the alternative, the microprocessor 2010 and/or the server(s) 2100 can send a first message to the patient's smartphone 2120 (e.g., a text message) or computer 2130 (e.g., an email). If it appears that the patient did not respond to the first alert or if the variance with the treatment plan is above a threshold (e.g., the patient did not perform any exercises over a predetermined time period such as a day or multiple days), the alert 2110 (e.g., a second alert) can include a light having a second color, intensity, and or blinking frequency, and it can further include an audible alert. In addition or in the alternative, the microprocessor 2010 and/or the server(s) 2100 can send a second message to the patient's smartphone 2120 (e.g., a text message) or computer 2130 (e.g., an email).

Figure 22:
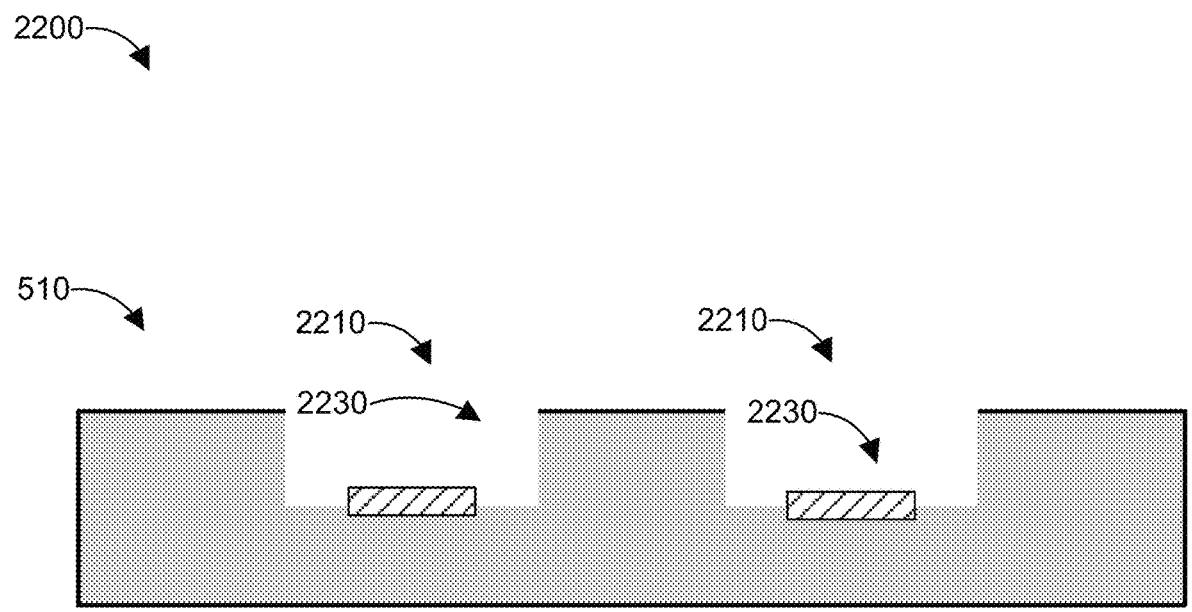
FIGS. 22, 23A, 23B, 24 and 25 are cross sections of the upper lid of the kit illustrated in FIG. 20, according to one or more embodiments.

FIG. 22 is a cross-section 2200 of the upper lid 510 of the housing 500 of kit 2000 through line A-A, as illustrated in FIG. 20, according to one or more embodiments. The wrap module 530B and the hot pack module 530F are not illustrated in FIG. 22 for clarity purposes only. The cross-section 2200 illustrates that the upper lid 510 includes a plurality of receptacles 2210 defined therein for receiving the hand therapy modules 530.

A module presence sensor 2230 is disposed in some or all of the recesses 2210. The module presence sensor 2230 changes its state when the corresponding hand therapy module 530 is removed from and/or returned to the receptacle 2210. The module presence sensor 2230 can include a light sensor and/or a weight or load sensor. The light sensor can function by detecting light when the hand therapy module 530 is removed from the receptacle 2210 and not detecting light when the hand therapy module 530 is disposed in the receptacle. Alternatively, the light sensor can include a light source in the receptacle 2210 and a reflective surface 2240 (e.g., a mirror) on the bottom of the hand therapy module 530 (or vice versa) such that the light sensor detects reflected light 2245 when the hand therapy module 530 is disposed in the receptacle, as illustrated in FIG. 23A, and does not detect any reflected light 2245 (e.g., having the intensity and/or wavelengths of the light emitted by the light source) when the when the hand therapy module 530 is removed from the receptacle 2210, as illustrated in FIG. 23B.

Figure 23A:
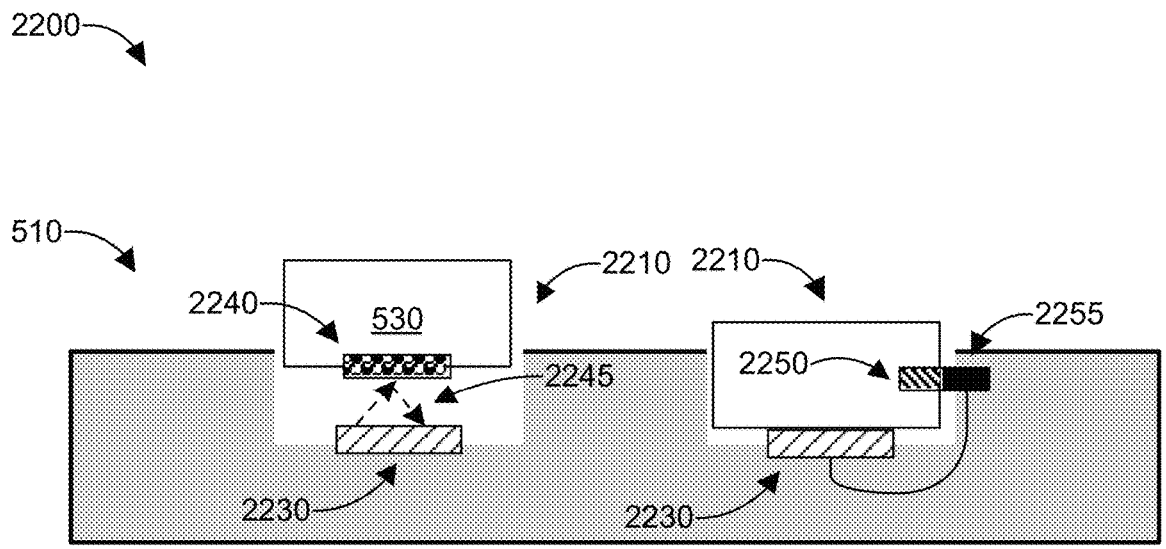
Figure 23B:
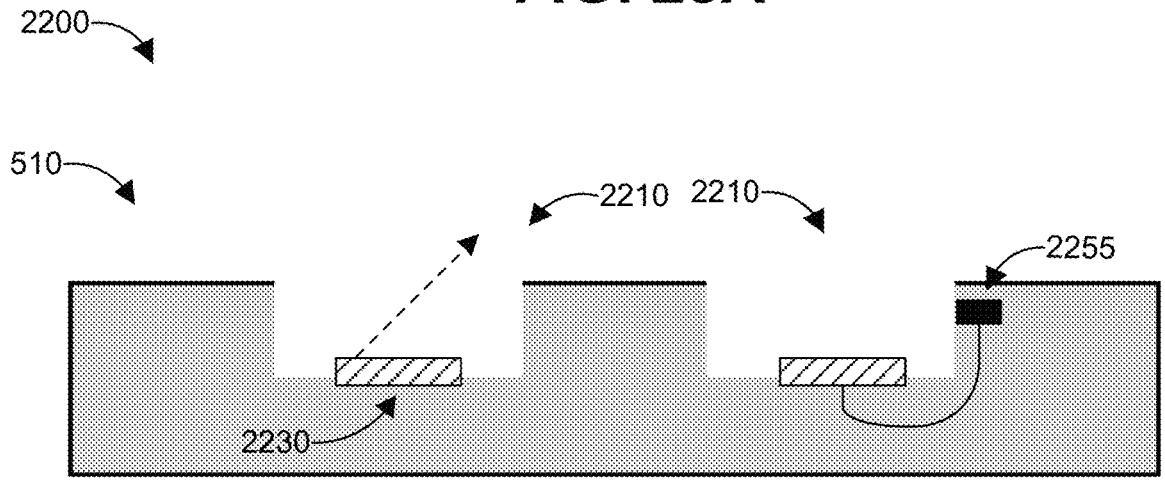

In addition or in the alternative, the module presence sensor 2230 can include a current sensor and/or a voltage sensor that can detect when an electrical connection is made between an electrode 2250 disposed on the hand therapy module 530 and an electrode 2255 disposed in the receptacle 2210 (e.g., on the bottom wall or on a sidewall), as illustrated in FIG. 23A. The electrical connection is broken when the hand therapy module 530 is removed from the receptacle 2210, as illustrated in FIG. 23B.

Figure 24:
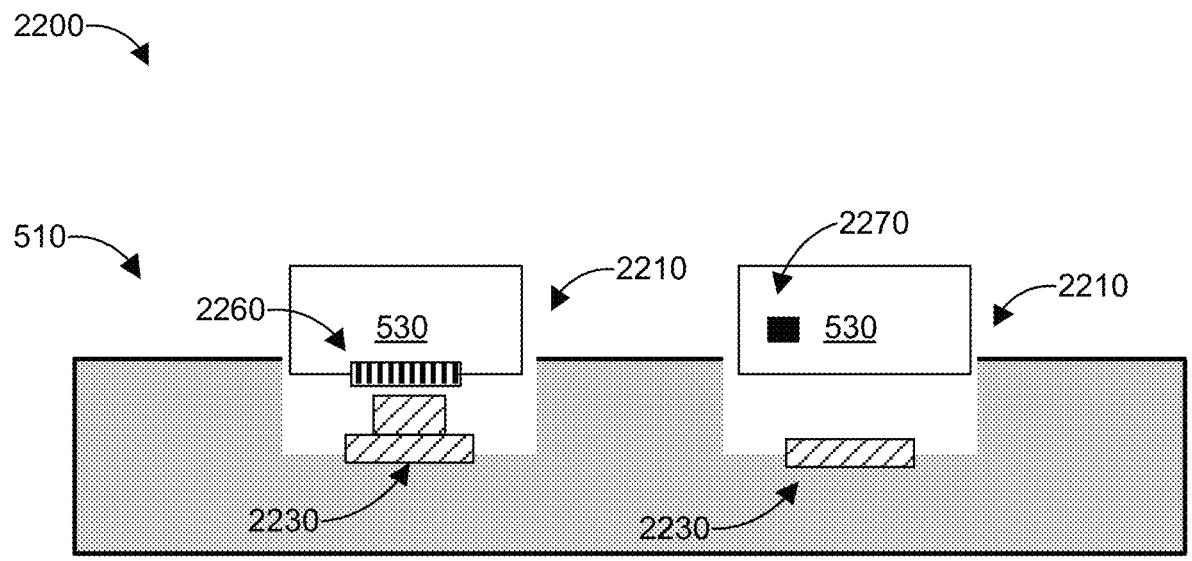

In addition or in the alternative, the module presence sensor 2230 can include a barcode reader that can read a barcode 2260, disposed on the hand therapy module 530, when the hand therapy module 530 is disposed in the receptacle 2210, as illustrated in FIG. 24. The hand therapy module 530 is disposed in the receptacle 2210 when the barcode reader can read the barcode on the hand therapy module 530, which can be read periodically or at regular or irregular intervals. When the barcode reader fails to read the barcode, the hand therapy module 530 has been removed from the receptacle 2210. The barcode can be unique to the hand therapy module 530, which can allow a computer in communication with the kit (e.g., kit 2000) to confirm which hand therapy module 530 has been removed or replaced.

In addition or in the alternative, the module presence sensor 2230 can include a radio-frequency identification (RFID) reader that can read (e.g., interrogate) an RFID tag 2270 disposed on or in the hand therapy module 530, as illustrated in FIG. 24. The RFID tag is within range of the RFID reader when the hand therapy module 530 is disposed in the receptacle 2210 and out of range when the hand therapy module 530 is removed from the receptacle 2210. The RFID tag can be unique to the hand therapy module 530, which can allow a computer in communication with the kit (e.g., kit 2000) to confirm which hand therapy module 530 has been removed or replaced.

Figure 25:
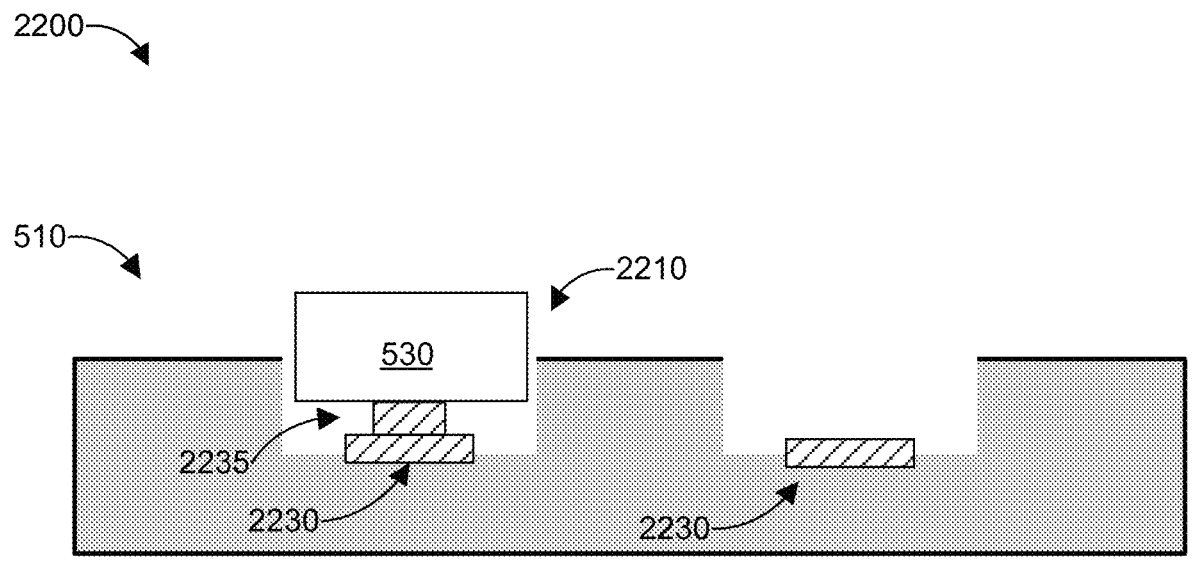

In addition or in the alternative, the module presence sensor 2230 can include a load sensor 2235 that can detect when weight is applied, as illustrated in FIG. 25. Thus, the load sensor 2235 can have a first state when then hand therapy module 530 in the receptacle 2210 (and on the load sensor) and a second state when the hand therapy module 530 is removed from the receptacle 2210.

The lower lid 520 can be configured the same as or different than the upper lid 510. For example, the lower lid 520 can include the receptacles 2210 the module presence sensors 2230, and/or the electrodes 2255 discussed above.

Figure 27:
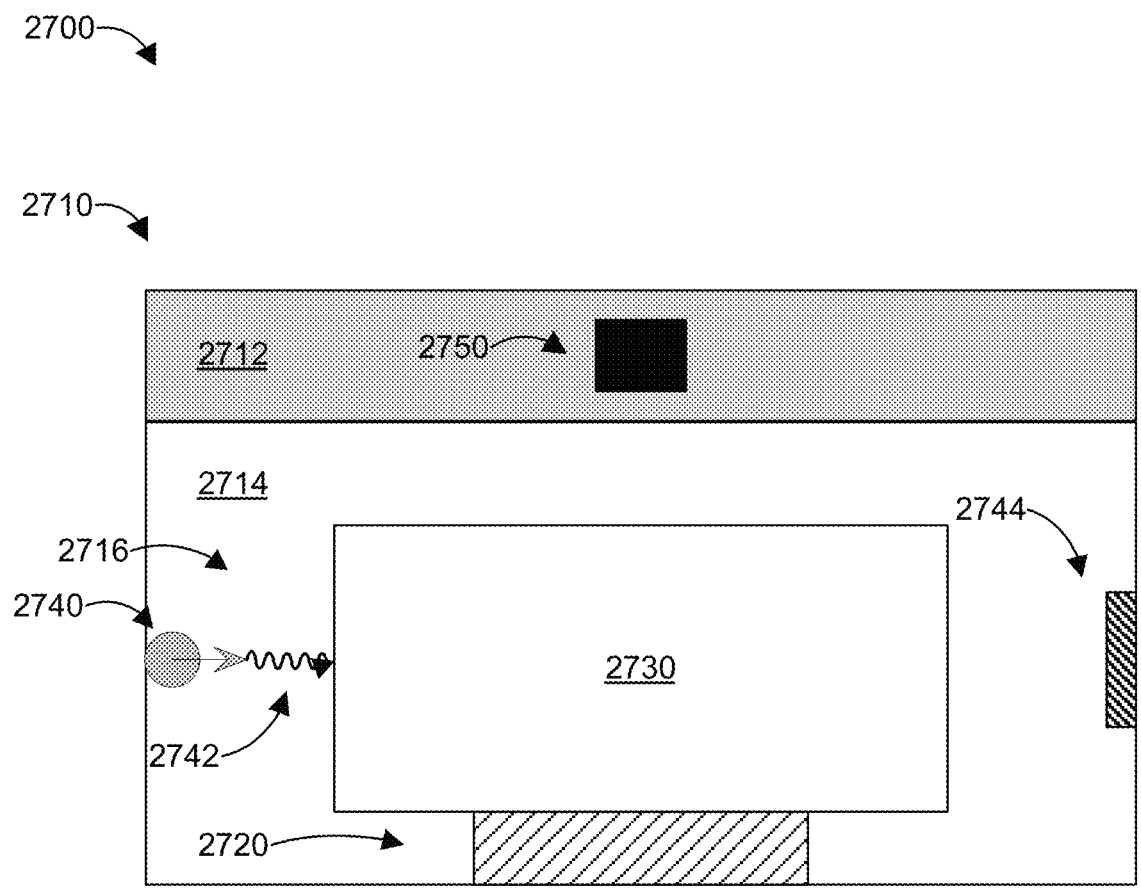
FIGS. 27 and 28 are side views of an assembly for detecting the presence of a hand therapy module according to one or more embodiments.
Figure 28:
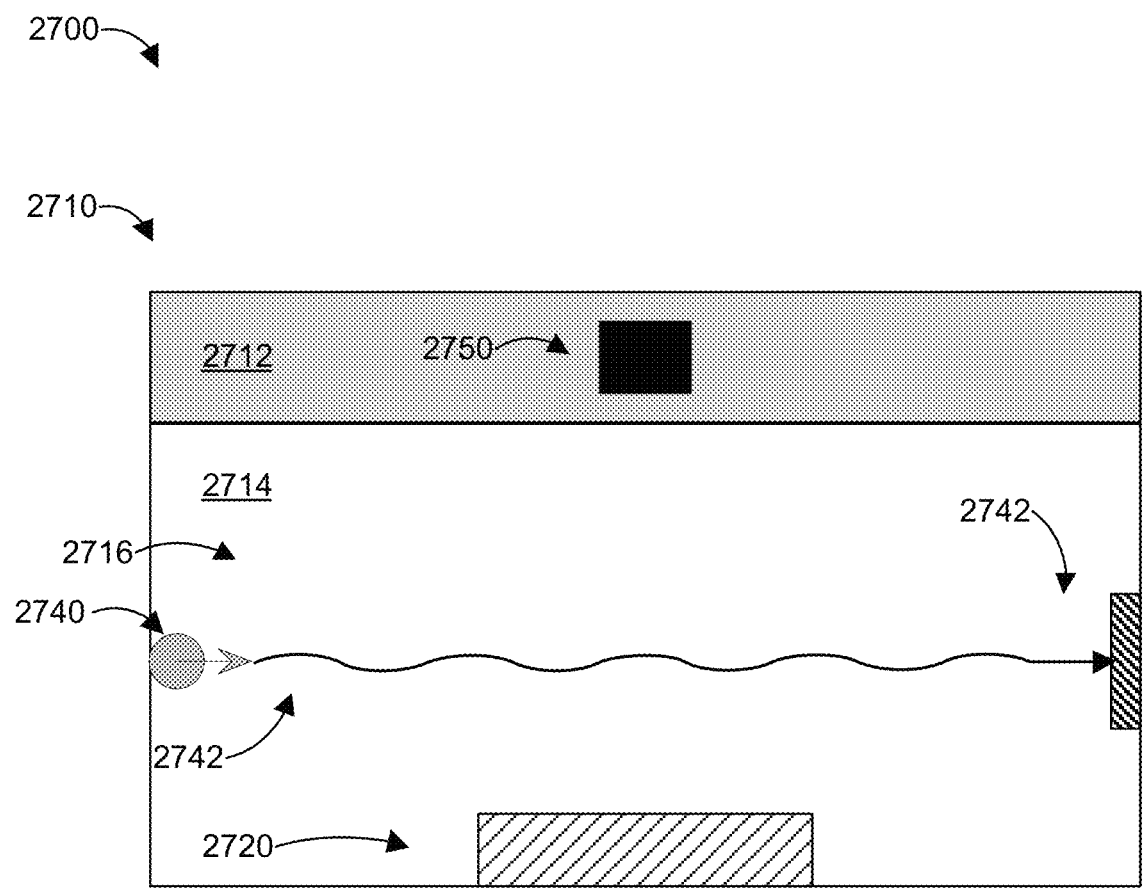

FIGS. 27 and 28 are side views of an assembly 2700 for detecting the presence of a hand therapy module according to one or more embodiments. The assembly 2700 includes a container 2710 that comprises a lid 2712 and a housing 2714. The lid 2712 is removably and/or rotatably coupled to the housing 2714 such that an internal cavity 2716 of the housing 2714 can be accessed from above. The internal cavity 2716 is configured and arranged to receive a hand therapy module 2730, which can be the same as or different than hand therapy module 530. The assembly 2700 can be disposed in the receptacle 2210, discussed above.

The hand therapy module 2730 is disposed on or near a container presence sensor 2720, which can be the same as or different than module presence sensor 2230. For example, the container presence sensor 2720 can include a light sensor, a weight or load sensor, a current sensor and/or a voltage sensor, a barcode reader, and/or an RFID reader. The container presence sensor 2720 can detect the presence or absence of the hand therapy module 2730 in the same way discussed above with respect to the module presence sensor 2230 and the hand therapy module 530, respectively. In addition or in the alternative, the container presence sensor 2720 can include a motion sensor.

In some embodiments, the container presence sensor 2720 optionally includes a light source 2740 (e.g., a laser, an LED, a fluorescent light, an incandescent light, or other light source) that emits light 2742 towards the hand therapy module 2730. The light from the light source 2740 is detected by a light detector 2744 when the hand therapy module 2730 is removed from the container 2710 (as illustrated in FIG. 28) but it is not detected by the light detector 2744 when the hand therapy module 2730 is disposed in the container 2710 (as illustrated in FIG. 27). Though the light source 2740 and light detector 2744 are illustrated as being disposed on the sidewalls of the housing 2714, it is noted that other positions are possible. For example, the light source 2740 can be disposed on the bottom of the housing and the light detector 2744 can be disposed on the bottom of the lid 2712 (or vice versa).

In some embodiments, a lid sensor 2750 is disposed on or in the lid 2712. The lid sensor 2750 can an accelerometer or other sensor that can detect whether the lid 2712 is opened or closed (or whether the lid is being opened or closed). The lid sensor 2750 can also include a current sensor and/or a voltage sensor that can sense when an electrode disposed on the lid 2712 is in electrical contact with an electrode disposed on the housing 2714, which occurs when the lid 2712 is closed but does not occur when the lid 2712 is opened. Thus the voltage and/or current in a circuit that includes the electrodes will be different depending on whether the electrodes are in electrical contact with each other.

Figure 29:
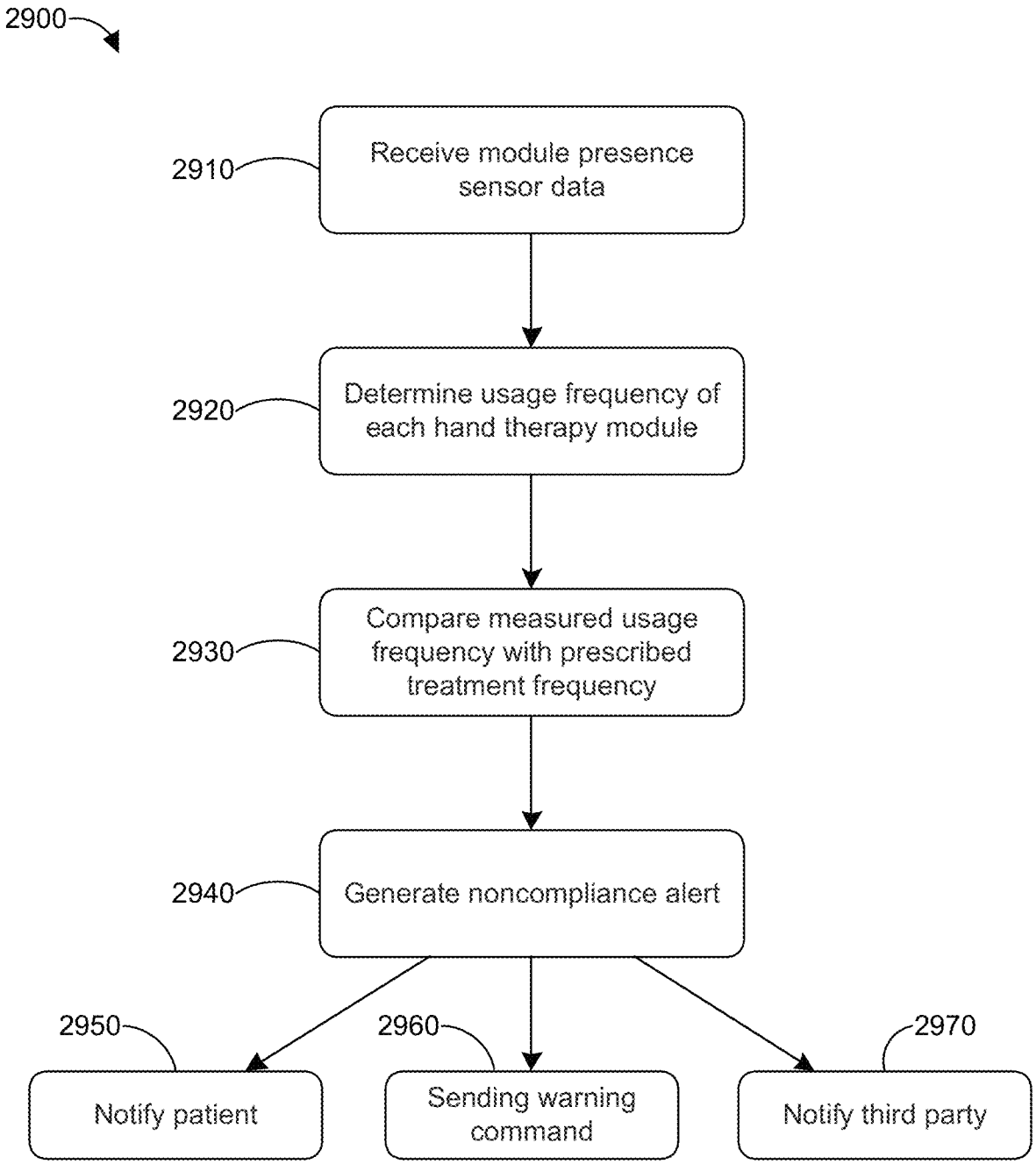
FIG. 29 is a flow chart of a computer-implemented method for remotely monitoring usage of removable hand therapy modules according to one or more embodiments.

FIG. 29 is a flow chart 2900 of a computer-implemented method for remotely monitoring usage of removable hand therapy modules according to one or more embodiments. In step 2910, a computer receives module presence sensor data that includes the state of each of a plurality of module presence sensors (e.g., module presence sensor 2230 and/or container presence sensor 2720). Each module presence sensor can be disposed in a corresponding receptacle, defined in a housing of a kit, that can removably receive a corresponding hand therapy module. In addition or in the alternative, each module presence sensor can be disposed in a container that can removably receive a corresponding hand therapy module. The state of each module presence sensor indicates whether the hand therapy module is disposed in the receptacle or container (and thus it is not in use) or whether the hand therapy module is disposed is removed from the receptacle or container (and thus may be in use).

In step 2920, the computer analyzes the module presence sensor data to determine a measured usage frequency of each hand therapy module. For example, if the sensor data indicates that a first hand therapy module has been removed and replaced three times during the day, the measured usage frequency is three times a day. In some embodiments, the computer can determine the measured usage frequencies using machine learning based on known sensor data of known usage frequencies. In some embodiments, the computer can generate an alarm and/or an error message if a hand therapy module was removed (e.g., from a corresponding receptacle) but not replaced after a predetermined time period (e.g., 30 minutes, 1 hour, 2 hours, or other time period).

In step 2930, the computer compares the measured usage frequency with a prescribed usage frequency that can be included in a treatment plan for the patient using the kit. If the measured usage frequency for a given hand therapy module is below the prescribed usage frequency for that hand therapy module, the computer can generate a noncompliance alert in step 2940. The noncompliance alert can result in notifying the patient in step 2950 (e.g., via a message such as an email, a text message, a telephone call, or other notification). In addition or in the alternative, the noncompliance alert can result in sending a warning command 2960 to a microprocessor disposed in the kit that causes the microprocessor to activate an alert module on the kit. For example, the alert module can include a light source, a speaker, and/or a screen. The warning command can cause the light source to generate a light having a predetermined wavelength and/or intensity, it can cause the speaker to generate a predetermined sound (e.g., a voice, a warning sound, or other sound), and/or it can cause the screen to display predetermined text, graphics, or images. In addition or in the alternative, the noncompliance alert can result in notifying a third party 2970 regarding the noncompliance. For example, the noncompliance alert can notify the patient's physical therapist that the patient is not complying with the treatment plan, including the detected reasons for noncompliance (e.g., in which hand therapy module is the measured usage frequency below the prescribed usage frequency, and what is the difference between the measured and prescribed usage frequencies). In another example, the noncompliance alert can notify an insurance company (e.g., the patient's health plan insurance company, a worker's compensation insurance company for the patient's employer, and/or another insurance company).

It is noted that the type and/or location of the sensors described herein can be modified as technology develops, as understood by those skilled in the art.

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A hand therapy kit comprising:
   a plurality of hand therapy modules;
   a housing that includes an upper lid and a lower lid, wherein said upper lid is removable from the lower lid to open said housing and said upper lid is engageable with the lower lid to close said housing, said upper and lower lids defining a plurality of receptacles to removably receive the hand therapy modules;
   a plurality of module presence sensors, each module presence sensor disposed in a respective receptacle and having a first state when a corresponding hand therapy module is disposed in the receptacle and a second state when the corresponding hand therapy module is removed from the receptacle; and
   a microprocessor disposed in the housing, the microprocessor in electrical communication with each module presence sensor to determine whether each module presence sensor is in the first state or in the second state.

2. The hand therapy kit of claim 1, wherein the microprocessor transmits module presence sensor data to a server through a communications interface disposed on or in the housing.

3. The hand therapy kit of claim 2, wherein the communications interface includes a wired communications interface, a wireless communications interface, or a combination thereof.

4. The hand therapy kit of claim 2, further comprising an alert module comprising a light source, a speaker, or a combination thereof, the alert module in electrical communication with the microprocessor to receive an alert command that activates at least one of the light source or the speaker.

5. The hand therapy kit of claim 1, wherein a first module presence sensor comprises a light sensor that receives a light emitted from a light source disposed in a first receptacle when the hand therapy module is removed from the first receptacle and that does not receive the light when the hand therapy module is disposed in the first receptacle.

6. The hand therapy kit of claim 1, wherein a first module presence sensor comprises a load sensor, disposed on a bottom of a first receptacle, to sense a weight when the hand therapy module is disposed in the first receptacle and to not sense the weight when the hand therapy module is removed from the first receptacle.

7. The hand therapy kit of claim 1, further comprising a first electrode disposed in a first receptacle and a second electrode disposed on an external surface of a first hand therapy module, the first and second electrodes are in electrical contact when the first hand therapy module is disposed in the first receptacle and the first and second electrodes are not in electrical contact when the first hand therapy module is removed from the first receptacle, and wherein a first module presence sensor comprises a voltage sensor, the voltage sensor sensing a first voltage in a circuit that includes the first and second electrodes when the first hand therapy module is disposed in the first receptacle, the voltage sensor sensing a second voltage in the circuit when the first hand therapy module is removed from the first receptacle.

8. The hand therapy kit of claim 1, wherein a first module presence sensor comprises a barcode reader disposed in a first receptacle and a barcode is disposed on an external surface of a first hand therapy module, the barcode reader reading the barcode when the first hand therapy module is disposed in the first receptacle, the barcode reader not reading the barcode when the first hand therapy module is removed from the first receptacle.

9. The hand therapy kit of claim 1, wherein a first module presence sensor comprises an RFID reader disposed in a first receptacle and an RFID tag is disposed on or in a first hand therapy module, the RFID reader reading the RFID tag when the first hand therapy module is disposed in the first receptacle, the RFID reader not reading the RFID tag when the first hand therapy module is removed from the first receptacle.

10. The hand therapy kit of claim 1, further comprising a memory operatively coupled to the microprocessor to store a status of each module presence sensor.

11. A hand therapy kit comprising:
a plurality of containers;
a plurality of hand therapy modules, each hand therapy module disposed in a respective container;
a plurality of container presence sensors, each container presence sensor disposed in a respective container and having a first state when a corresponding hand therapy module is disposed in the container and a second state when the corresponding hand therapy module is removed from the container; and
a microprocessor in electrical communication with each container presence sensor to determine whether each container presence sensor is in the first state or in the second state.

12. The hand therapy kit of claim 11, wherein the microprocessor transmits container presence sensor data to a server through a communications interface disposed on or in the housing.

13. The hand therapy kit of claim 12, wherein the communications interface includes a wired communications interface, a wireless communications interface, or a combination thereof.

14. The hand therapy kit of claim 12, further comprising an alert module comprising a light source, a speaker, or a combination thereof, the alert module in electrical communication with the microprocessor to receive an alert command that activates at least one of the light source or the speaker.

15. The hand therapy kit of claim 11, wherein a first container presence sensor comprises a light sensor disposed that receives a light emitted from a light source when the hand therapy module is removed from a first receptacle and that does not receive the light when the hand therapy module is disposed in the first receptacle, the light sensor and the light source on opposite sides of the container.

16. The hand therapy kit of claim 11, wherein a first module presence sensor comprises a load sensor, disposed on a bottom of a first container, to sense a weight when the hand therapy module is disposed in the first container and to not sense the weight when the hand therapy module is removed from the first container.

17. The hand therapy kit of claim 11, further comprising a first electrode disposed in a first container and a second electrode disposed on an external surface of a first hand therapy module, the first and second electrodes are in electrical contact when the first hand therapy module is disposed in the first container and the first and second electrodes are not in electrical contact when the first hand therapy module is removed from the first container, and wherein a first container presence sensor comprises a voltage sensor, the voltage sensor sensing a first voltage in a circuit that includes the first and second electrodes when the first hand therapy module is disposed in the first container, the voltage sensor sensing a second voltage in the circuit when the first hand therapy module is removed from the first container.

18. The hand therapy kit of claim 11, wherein a first container presence sensor comprises a barcode reader disposed in a first container and a barcode is disposed on an external surface of a first hand therapy module, the barcode reader reading the barcode when the first hand therapy module is disposed in the first container, the barcode reader not reading the barcode when the first hand therapy module is removed from the first container.

19. The hand therapy kit of claim 11, wherein a first module presence sensor comprises an RFID reader disposed in a first container and an RFID tag is disposed on or in a first hand therapy module, the RFID reader reading the RFID tag when the first hand therapy module is disposed in the first container, the RFID reader not reading the RFID tag when the first hand therapy module is removed from the first container.

20. The hand therapy kit of claim 11, further comprising a memory operatively coupled to the microprocessor to store a status of each container presence sensor.

21. The hand therapy kit of claim 11, further comprising a housing that defines a plurality of receptacles, each container disposed in a corresponding receptacle.

22. The hand therapy kit of claim 11, further comprising a plurality of lid sensors, each lid sensor in electrical communication with the microprocessor, wherein each container includes a lid removably disposed on a housing, and a respective lid sensor is disposed on each lid, each lid sensor having a first state when the lid is opened and a second state when the lid is closed.

23. A computer-implemented method for remotely monitoring a usage of removable hand therapy modules, comprising:
in a computer:
receiving module presence sensor data that includes a state of each of a plurality of module presence sensors, each module presence sensor disposed in a corresponding receptacle defined in a housing of a kit, each module presence sensor having a first state when a corresponding hand therapy module is disposed in the corresponding receptacle and a second state when the corresponding hand therapy module is removed from the corresponding receptacle;
analyzing the module presence sensor data to determine a measured usage frequency of each hand therapy module;
comparing the measured usage frequency of each hand therapy module to a treatment plan, the treatment plan including a prescribed usage frequency for each hand therapy module; and
generating a noncompliance alert when the measured usage frequency of at least one hand therapy module is lower than the prescribed usage frequency.

24. The method of claim 23, wherein each module presence sensor is disposed in a corresponding receptacle defined in a kit housing.

25. The method of claim 23, wherein each module presence sensor is disposed in a container.

26. The method of claim 23, further comprising sending an alert message to a third party, the alert message including the noncompliance alert.

27. The method of claim 26, wherein the third party includes a physical therapist, an insurance agency, or both the physical therapist and the insurance agency.

28. The method of claim 23, further comprising sending a warning command to the kit, the kit comprising a microprocessor and an alert module in electrical communication therewith, the warning command causing the microprocessor to activate the alert module, the alert module including a light source, a speaker, or both the light source and the speaker.

29. The method of claim 28, further comprising sending a warning message to a patient associated with the kit, the warning message indicating a detected variance from the treatment plan.

* * * * *